(12) United States Patent
Allison et al.

(10) Patent No.: US 10,470,813 B2
(45) Date of Patent: Nov. 12, 2019

(54) METHODS AND SYSTEMS FOR PREVENTING NEUROMA FORMATIONS

(71) Applicant: Pacira CryoTech, Inc., Parsippany, NJ (US)

(72) Inventors: John Allison, Los Altos, CA (US); Jessica Preciado Dummett, Dublin, CA (US); Michael Hsu, Fremont, CA (US)

(73) Assignee: Pacira CryoTech, Inc., Parsippany, NJ (US)

( * ) Notice: Subject to any disclaimer, the term of this patent is extended or adjusted under 35 U.S.C. 154(b) by 503 days.

(21) Appl. No.: 15/069,790

(22) Filed: Mar. 14, 2016

(65) Prior Publication Data

US 2016/0262820 A1 Sep. 15, 2016

Related U.S. Application Data

(60) Provisional application No. 62/132,238, filed on Mar. 12, 2015.

(51) Int. Cl.
*A61B 18/02* (2006.01)
*A61B 18/00* (2006.01)
*A61B 90/00* (2016.01)

(52) U.S. Cl.
CPC .... *A61B 18/02* (2013.01); *A61B 2018/00434* (2013.01); *A61B 2018/0293* (2013.01);
(Continued)

(58) Field of Classification Search
CPC .......... A61B 18/02; A61B 2018/00434; A61B 2018/0293; A61B 2090/3925; A61B 2090/3937
(Continued)

(56) References Cited

U.S. PATENT DOCUMENTS

| 4,802,475 A | * | 2/1989 | Weshahy | A61B 18/0218 128/DIG. 27 |
| 5,409,004 A | * | 4/1995 | Sloan | A61B 6/502 600/434 |

(Continued)

FOREIGN PATENT DOCUMENTS

| WO | 2010/075438 | 7/2010 |
| WO | 2010/075448 | 7/2010 |

OTHER PUBLICATIONS

The American Orthopaedic Foot & Ankle Society (AOFAS). "Below-Knee Amputation." American Orthopaedic Foot & Ankle Society, Mar. 3, 2015. file:///H:/Patent%20Applications/15069790/03-03-201Below-Knee%20Amputation.html.*
(Continued)

*Primary Examiner* — Ronald Hupczey, Jr.
*Assistant Examiner* — Christine A Dedoulis
(74) *Attorney, Agent, or Firm* — Kilpatrick Townsend and Stockton LLP

(57) ABSTRACT

The present invention generally relates to improved medical devices, systems, and methods. In many embodiments, devices, systems, and methods for amputating a limb of a patient are provided. In many embodiments, devices, systems, and methods may provide chronic denervation of one or more nerves of a patient as part of a therapeutic treatment. The methods may employ cold for the prevention of neuromas or fibromas associated with amputation of a limb of a patient. Embodiments of the invention include needles that can be advanced through skin or other tissues to cause axonotmesis of a target nerve of the patient and to repeatedly interrupt a regeneration of the nerve so as to provide therapeutic chronic denervation of the target nerve. The therapeutic chronic denervation may delay the formation of neuromas or fibromas in a patient's residual limb and/or may
(Continued)

provide long lasting and permanent pain relief associated with the target nerve.

30 Claims, 22 Drawing Sheets

(52) U.S. Cl.
CPC ............... *A61B 2090/3925* (2016.02); *A61B 2090/3937* (2016.02)

(58) Field of Classification Search
USPC ...................................................... 607/104
See application file for complete search history.

(56) References Cited

U.S. PATENT DOCUMENTS

| | | | |
|---|---|---|---|
| 7,250,046 B1* | 7/2007 | Fallat ................... | A61B 18/02 128/898 |
| 7,713,266 B2 | 5/2010 | Elkins et al. | |
| 7,850,683 B2 | 12/2010 | Elkins et al. | |
| 8,298,216 B2 | 10/2012 | Burger et al. | |
| 8,409,185 B2 | 4/2013 | Burger et al. | |
| 9,039,688 B2 | 5/2015 | Palmer, III et al. | |
| 9,254,162 B2 | 2/2016 | Elkins et al. | |
| 2003/0040112 A1* | 2/2003 | Muir ..................... | A61K 38/51 435/368 |
| 2009/0299357 A1 | 12/2009 | Zhou | |
| 2010/0198207 A1 | 8/2010 | Elkins et al. | |
| 2012/0089211 A1 | 4/2012 | Curtis et al. | |
| 2014/0343542 A1 | 11/2014 | Karnik et al. | |
| 2015/0066007 A1* | 3/2015 | Srivastava ..... | A61B 17/320068 606/21 |
| 2016/0058502 A1* | 3/2016 | Clark ................ | A61B 18/1492 606/41 |

OTHER PUBLICATIONS

Ellen E. Rhame, Alexander F. DeBonet, and Thomas T. Simopoulos, "Ultrasonographic Guidance and Characterization of Cryoanalgesic Lesions in Treating a Case of Refractory Sural Neuroma," Case Reports in Anesthesiology, vol. 2011, Article ID 691478, 4 pages, 2011. https://doi.org/10.1155/2011/691478.*

Moesker et al. (2012). Treatment of Phantom Limb Pain by Cryoneurolysis of the Amputated Nerve. Pain Practice, vol. 14(1): 52-56.*

U.S. Appl. No. 61/116,050, filed Nov. 19, 2008.

Jonsson et al., "Effect of Delayed Peripheral Nerve Repair on Nerve Regeneration, Schwann Cell Function and Target Muscle Recovery", PLOS ONE, vol. 8, Issue 2, e56484, Feb. 2013, pp. 1-13.

Sulaiman, MD, PHD, FRCS et al., "Neurobiology of Peripheral Nerve Injury, Regeneration, and Functional Recovery: From Bench Top Research to Bedside Application", The Ochsner Journal, vol. 13, No. 1, 2013, pp. 100-108.

* cited by examiner

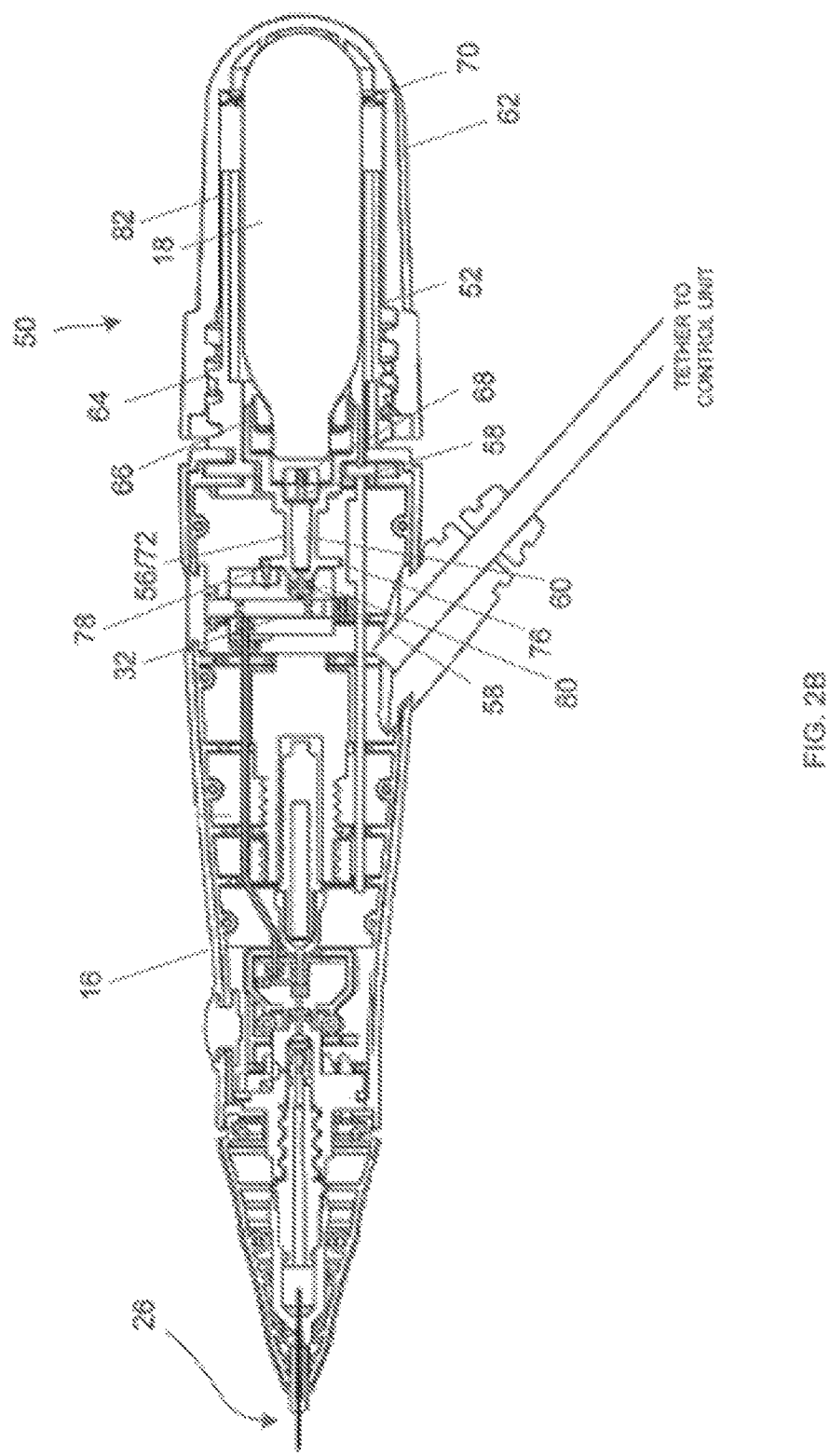

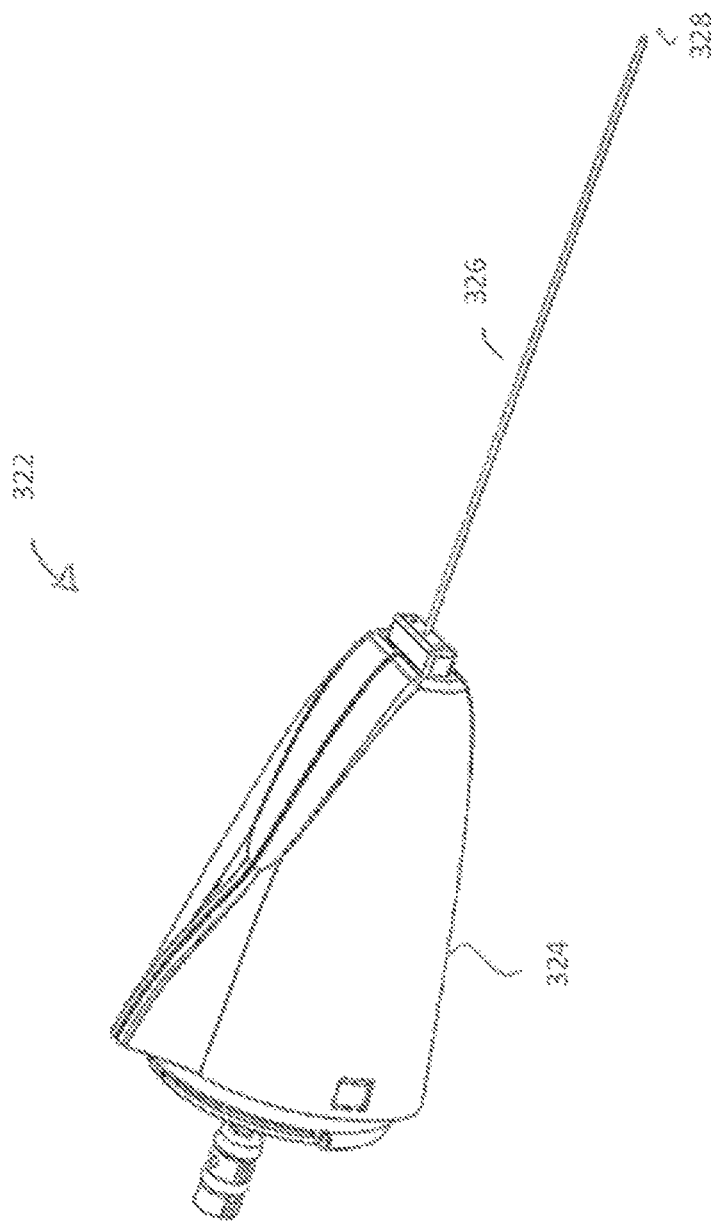

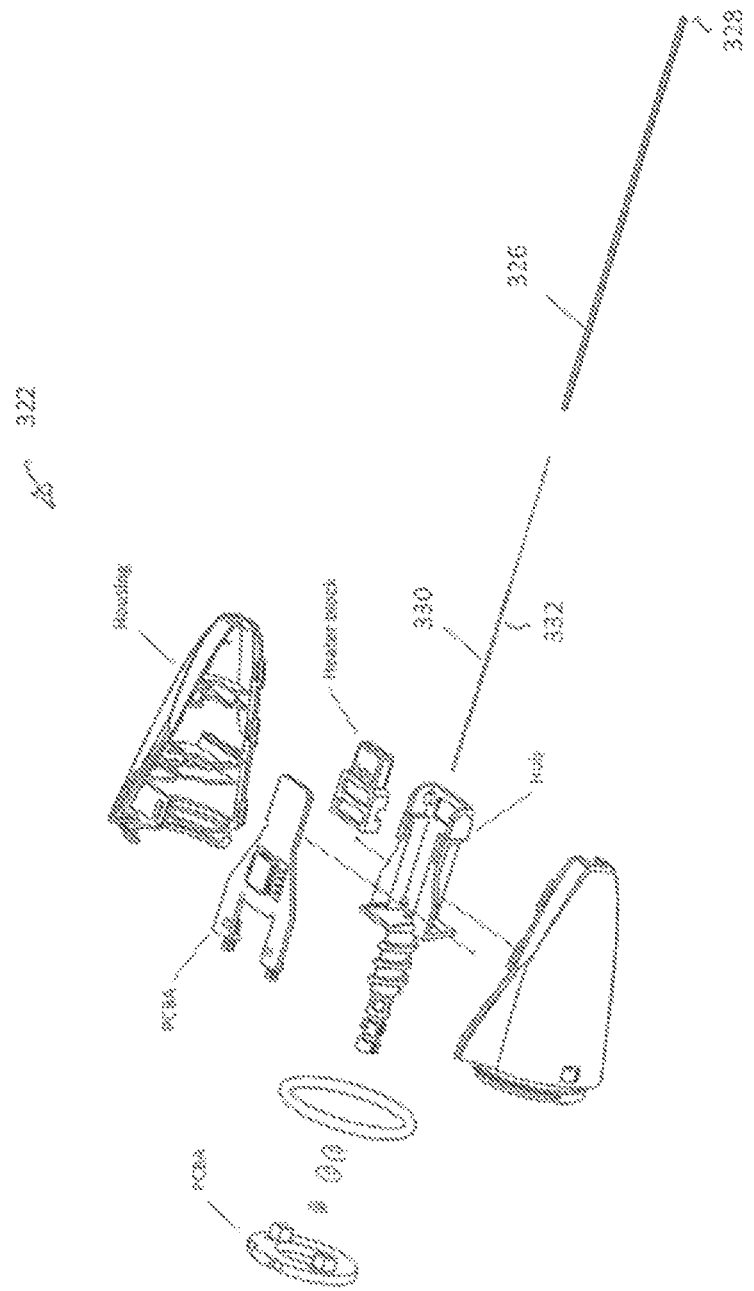

though disclosure is incorporated herein by reference in its

METHODS AND SYSTEMS FOR PREVENTING NEUROMA FORMATIONS

CROSS REFERENCE TO RELATED APPLICATION DATA

The present application claims the benefit of U.S. Provisional Appln. No. 62/132,238 filed Mar. 12, 2015; the full disclosure which is incorporated herein by reference in its entirety for all purposes.

BACKGROUND

The present invention generally relates to improved medical devices, systems, and methods. In many embodiments, devices, systems, and methods for preventing neuroma formations associated with amputating a limb of a patient are provided.

Amputation is the surgical removal of all or part of a limb or extremity such as an arm, leg, foot, hand, toe, or finger. An estimated 1.8 million Americans are living with amputations and approximately 185,000 amputations occur in the United States each year. Amputation of the leg, either above or below the knee, is the most common amputation surgery.

During an amputation procedure, the portion of nerves extending distally from the amputation level must be transected. Neuroma formation at the transection site is a natural consequence of the transection and thus amputees may have several neuromas form in their residual limb after the amputation procedure. These neuromas may produce mild discomfort to the amputee or, in more severe cases, may produce continuous and/or severe pain. Some prosthetics may be designed such that the socket accommodates neuromas by avoiding weight bearing or other significant pressure on the neuroma during prosthetic use. While this may be sufficient in some instances, in others, the neuroma may form at locations, such as bony prominences, where pressure from use with or without a prosthesis is unavoidable (e.g., metacarpal heads, at the neck of the fibula, etc.). Accordingly, it would be desirable to provide methods and systems for preventing neuroma formation associated with amputating a limb or extremity of a patient to address such issues as patient discomfort and/or pain. For example, methods and systems which reduce or prevent the formation of neuromas after amputation may be advantageous.

SUMMARY OF THE INVENTION

The present invention generally relates to improved medical devices, systems, and methods. In many embodiments, devices, systems, and methods for reducing or preventing the formation of neuromas associated with nerve transection during a medical intervention such as limb amputation or other surgical procedures are provided. The methods and devices may be beneficial for other exemplary interventions in addition to amputation, such as general thoracic surgeries where surgeons gain access between two or more ribs to the chest cavity. Additionally, surgeries involving the heart and major vessels, upper lung, and esophagus may benefit from the methods and devices disclosed herein to therapeutically treat nerves, reduce a regeneration of a nerve, induce chronic denervation, and/or prevent or reduce neuroma formation at a transected end of the nerve.

In many embodiments, improved devices, systems, and methods for transecting a nerve (e.g., during amputation of a limb or the like) may provide chronic denervation of one or more nerves of a patient as part of a therapeutic treatment.

The therapeutic treatment may reduce or prevent neuroma formation in at a transected end of the nerve or in a residual limb of an amputee in the case of an amputation. The prophylactic methods of the present invention may employ cold therapy for the prevention of neuromas or fibromas associated with an amputation of a limb of a patient. Embodiments of the invention include cryogenic cooling needles that can be advanced through skin or other tissues to cause axonotmesis of a target nerve of the patient and to repeatedly interrupt a regeneration of the nerve so as to provide therapeutic chronic denervation of the target nerve for preventing neuroma formation by a transected or injured nerve. The therapeutic chronic denervation may prevent the formation of neuromas or fibromas in a residual limb of the patient and/or may provide long lasting and permanent pain relief associated with the target nerve.

In some embodiments, a method of amputation may be provided. The method may prevent neuroma formation in nerve tissue associated with surgical amputation of a body extremity of a patient. The method may include identifying a nerve extending across a cutting path which separates the body extremity from a body of the patient. A cooling therapy may be administered to the identified nerve at a location proximal to the cutting path so as to degenerate the identified nerve across the cutting path prior to, during, or within a predetermined time period after surgically cutting along the cutting path to separate the body extremity from the body of the patient and to transect the identified nerve. The cooling of the identified nerve may prevent or reduce neuroma formation in a residual limb of the patient that remains after amputation.

Optionally, the method may start with the planning of a cutting path at an amputation level to separate the body extremity from a body of the patient. A nerve extending across the planned cutting path or an amputation level may be identified and a cooling therapy may be administered to the identified nerve at a location proximal to the planned cutting path so as to degenerate the identified nerve across the cutting path. After degenerating the identified nerve by administering the cooling therapy, the method may include cutting along the planned cutting path to separate the body extremity from the body of the patient and transecting the identified nerve. The application of cooling therapy prior to, during, or shortly after cutting along the planned cutting path may reduce neuroma formation in a residual stump of the patient that remains after removal of the body extremity of the patient.

The method may further include administering a repeated application of cooling therapy targeting a regeneration of the identified nerve at one or more locations proximal to the stump of the patient prior to the regeneration extending to a location of the transection of the identified nerve. The repeated application may reduce an expression of nerve growth factors. The repeated application of cooling therapy may repeatedly disrupt the regeneration of an axon of the identified nerve. The repeated application of cooling therapy to disrupt the regeneration of the identified nerve may induce chronic denervation of the identified nerve. The chronic denervation of the identified nerve may reduce a regenerative rate of the identified nerve. In some embodiments, the regenerative rate of the identified nerve may be reduced to less than 1 mm per day, to less than 0.5 mm per day, to less than 0.1 mm per day, less than 0.05 mm per day, or permanently disrupted by the chronic denervation (i.e., approximately 0 mm per day).

In some embodiments, administering the cooling therapy to the nerve may include positioning a needle of a cryotherapy probe across the identified nerve, aligning visual indicia of the needle of the cryotherapy probe with the nerve (the visual indicial may be indicative of a treatment area along a length of the needle), and activating the cryotherapy probe to deliver the cooling therapy. The visual indicia may be a marking identifying a distal end of the treatment area along the length of the needle. Optionally, the visual indicia may be a marking identifying a proximal end of the treatment area along the length of the needle and/or a marking identifying a center of the treatment area along the length of the needle. In some embodiments, the length of the needle may be 10 cm or more. In some embodiments, the cooling therapy may be administered to the nerve without medical imaging. Administering the cooling therapy to the nerve may be performed by positioning a needle of a cryotherapy probe along a length of the identified nerve and activating the cryotherapy probe to deliver the cooling therapy. The identified nerve may be a peripheral nerve. The identified nerve may be a sensory nerve.

In some embodiments, the repeated application of cooling therapy may be administered over a period of one month to three months before or after the transection of the nerve. The repeated application of cooling therapy may be administered between a daily interval and a four week interval.

In some embodiments, a cryotherapy probe may be provided. The cryotherapy probe may include a handle for holding by an operator and a needle extending distally from the handle. The needle may have a proximal end, a distal end, and a length therebetween. The needle may be configured to produce a cooling therapy zone along the length of the needle when the cryotherapy probe is activated to administer a cooling therapy. The needle may include at least one visible mark along the length of the needle to indicate at least one of a distal end, a proximal end, and a center of the cooling therapy zone produced when the cryotherapy probe is activated to administer the cooling therapy.

The needle may include visible marks for each of the distal end, the proximal end, and the center of the cooling therapy zone produced when the cryotherapy probe is activated to administer the cooling therapy. The length of the needle may be 10 cm or more. The cryotherapy probe needle may further include visible marks identifying a distance from the distal end of the needle.

In further aspects of the present invention, a method of transecting a nerve extending to a target tissue is provided. The method may include treating the nerve by degenerating the nerve at a location along the nerve to degenerate an axon of the nerve while preserving a connective tissue framework of the nerve. The preserved connective tissue framework of the nerve may be transected at a location distal to the location where degeneration was induced. A regeneration of the nerve may be repeatedly disrupted over a period of time so as to induce chronic denervation of the nerve. The chronic denervation of the nerve may reduce a regenerative rate of the nerve. The chronic denervation may prevent neuroma formation at the transection location of the nerve. Optionally, repeatedly disrupting the regeneration of the nerve comprises repeatedly applying cooling therapy to the nerve at a location proximal to the target tissue. The repeated application of cooling therapy may be administered over a period of one month to three months after the transection of the nerve. Optionally, the repeated application of cooling therapy may be applied between a daily interval and a four week interval (e.g., at one week intervals).

The method may further include selecting an interval for the repeated application of cooling therapy based on a distance from the location where degeneration was induced to the target tissue. A shorter interval may be selected as the distance decreases and longer intervals may be selected as the distance increases. The repeated application of cooling therapy may reduce an expression of nerve growth factors. In some embodiments, the repeated application of cooling therapy may reduce a regeneration rate of the nerve.

Other energy based therapies that induce axonotmesis while avoiding disruption of the connective nervous tissue along the nerve pathway may be used in the alternative to cooling therapy. Examples of such energy based therapies would include forms of radiofrequency, microwave, ultrasound, laser, etc. Preferably, the energy based therapy induces axonotmesis and avoids disrupting the connective nerve tissue.

In any of the embodiments disclosed herein, the one or more needles may include a coating that enhances visibility of the needle in ultrasound imaging. The coating may be along the entire length of the needle. In some embodiments, the coating may be only at the at least one visible mark along the length of the needle. Optionally, the coating may be along the entire length of the needle except for at the at least one visible mark along the length of the needle. In some embodiments, the coating may be along the length of the needle and terminates at the center of the cooling therapy zone such that a distal end of the coating is associated with the center of the cooling therapy zone.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

The invention will be better understood on reading the following description and examining the figures that accompany it. These figures are provided by way of illustration only and are in no way limiting on the invention.

BRIEF DESCRIPTION OF THE DRAWINGS

Further details, aspects and embodiments of the invention will be described by way of example only and with reference to the drawings. In the drawings, like reference numbers are used to identify like or functionally similar elements. Elements in the figures are illustrated for simplicity and clarity and have not necessarily been drawn to scale.

FIG. 2B is a cross-sectional view of the system of FIG. 1A, according to some embodiments of the invention;

FIGS. 3A-3E illustrate exemplary embodiments of needle probes, according to some embodiments of the invention;

DETAILED DESCRIPTION

The present invention provides improved medical devices, systems, and methods. More particularly, the prophylactic methods and devices of the present invention may employ cold therapy for the prevention of neuromas or fibromas associated with an amputation of a limb of a patient. Embodiments of the invention may treat target tissues disposed at and below the skin, optionally to treat pain associated with a sensory nerve. Embodiments of the invention may utilize a handheld refrigeration system that can use a commercially available cartridge of fluid refrigerant. Refrigerants well suited for use in handheld refrigeration systems may include nitrous oxide and carbon dioxide. These can achieve temperatures approaching −90° C.

Sensory nerves and associated tissues may be temporarily impaired using moderately cold temperatures of 10° C. to −5° C. without permanently disabling the tissue structures. Using an approach similar to that employed for identifying structures associated with atrial fibrillation, a needle probe or other treatment device can be used to identify a target tissue structure in a diagnostic mode with these moderate temperatures, and the same probe (or a different probe) can also be used to provide a longer term or permanent treatment, optionally by treating the target tissue zone and/or inducing apoptosis at temperatures from about −5° C. to about −50° C. In some embodiments, apoptosis may be induced using treatment temperatures from about −1° C. to about −15° C., or from about −1° C. to about −19° C., optionally so as to provide a longer lasting treatment that limits or avoids inflammation and mobilization of skeletal muscle satellite repair cells. In some embodiments, axonotmesis with Wallerian degeneration of a sensory nerve is desired, which may be induced using treatment temperatures from about −20° C. to about −100° C. Hence, the duration of the treatment efficacy of such subdermal cryogenic treatments may be selected and controlled, with colder temperatures, longer treatment times, and/or larger volumes or selected patterns of target tissue determining the longevity of the treatment. Additional description of cryogenic cooling methods and devices may be found in commonly assigned U.S. Pat. No. 7,713,266 entitled "Subdermal Cryogenic Remodeling of Muscle, Nerves, Connective Tissue, and/or Adipose Tissue (Fat)", U.S. Pat. No. 7,850,683 entitled "Subdermal Cryogenic Remodeling of Muscles, Nerves, Connective Tissue, and/or Adipose Tissue (Fat)", U.S. Pat. No. 9,039,688 entitled "Method for Reducing Hyperdynamic Facial Wrinkles", and U.S. Pat. No. 8,298,216 entitled "Pain Management Using Cryogenic Remodeling," the full disclosures of which are each incorporated by reference herein.

Figure 1A:
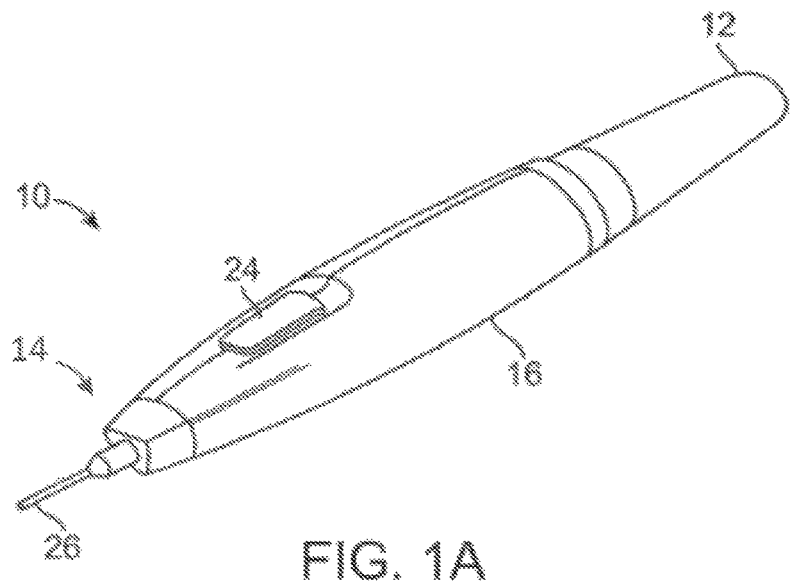
FIG. 1A is a perspective view of a self-contained subdermal cryogenic probe and system, according to some embodiments of the invention.
Figure 1B:
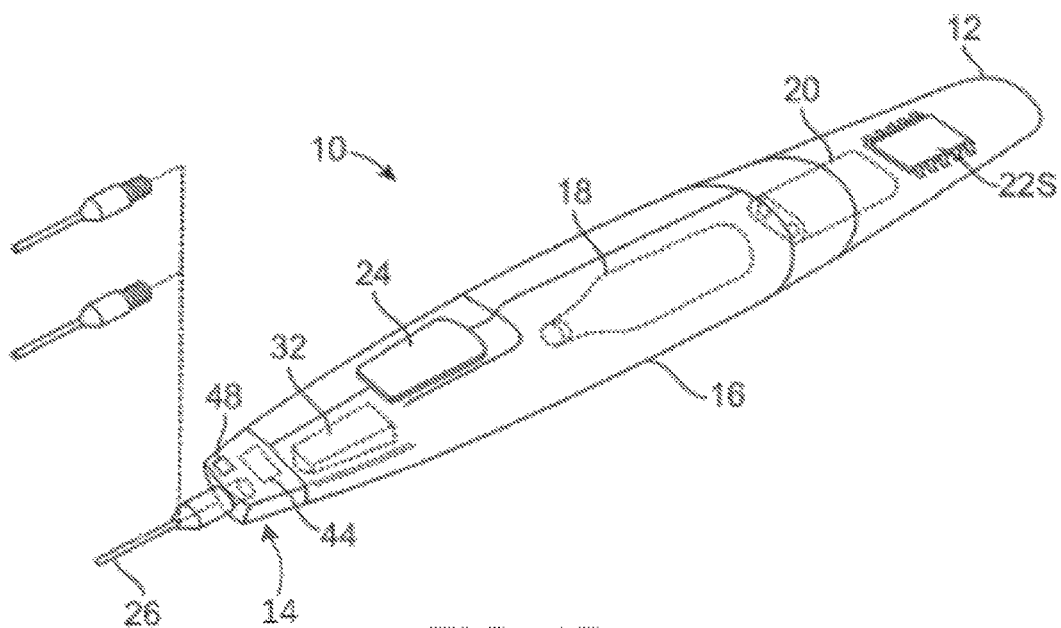
FIG. 1B is a partially transparent perspective view of the self-contained probe of FIG. 1A, showing internal components of the cryogenic system and schematically illustrating replacement treatment needles for use with the disposable probe according to some embodiments of the invention.

Referring now to FIGS. 1A and 1B, a system for cryogenic remodeling here comprises a self-contained probe handpiece generally having a proximal end 12 and a distal end 14. A handpiece body or housing 16 has a size and ergonomic shape suitable for being grasped and supported in a surgeon's hand or other system operator. As can be seen most clearly in FIG. 1B, a cryogenic cooling fluid supply 18, a supply valve 32 and electrical power source 20 are found within housing 16, along with a circuit 22S having a processor for controlling cooling applied by self-contained system 10 in response to actuation of an input 24. Alternatively, electrical power can be applied through a cord from a remote power source. Power source 20 also supplies power to heater element 44 in order to heat the proximal region of probe 26 which may thereby help to prevent unwanted skin damage, and a temperature sensor 48 adjacent the proximal region of probe 26 helps monitor probe temperature. Additional details on the heater 44 and temperature sensor 48 are described in greater detail below. When actuated, supply valve 32 controls the flow of cryogenic cooling fluid from fluid supply 18. Some embodiments may, at least in part, be manually activated, such as through the use of a manual supply valve and/or the like, so that processors, electrical power supplies, and the like may not be required.

Extending distally from distal end 14 of housing 16 may be a tissue-penetrating cryogenic cooling probe 26. Probe 26 is thermally coupled to a cooling fluid path extending from cooling fluid source 18, with the exemplary probe comprising a tubular body receiving at least a portion of the cooling fluid from the cooling fluid source therein. The exemplary probe 26 may comprise a 30 G needle having a sharpened distal end that is axially sealed. Probe 26 may have an axial length between distal end 14 of housing 16 and the distal end of the needle of between about 0.5 mm and 15 cm. Such needles may comprise a stainless steel tube with an inner diameter of about 0.006 inches and an outer diameter of about 0.012 inches, while alternative probes may comprise structures having outer diameters (or other lateral cross-sectional dimensions) from about 0.006 inches to about 0.100 inches. Generally, needle probe 26 may comprise a 16 g or smaller size needle, often comprising a 20 g needle or smaller, typically comprising a 25, 26, 27, 28, 29, or 30 g or smaller needle.

In some embodiments, probe 26 may comprise two or more needles arranged in a linear array, such as those disclosed in previously incorporated U.S. Pat. No. 7,850,683. Another exemplary embodiment of a probe having multiple needle probe configurations allow the cryogenic treatment to be applied to a larger or more specific treatment area. Other needle configurations that facilitate controlling the depth of needle penetration and insulated needle embodiments are disclosed in commonly assigned U.S. Pat. No. 8,409,185 entitled "Replaceable and/or Easily Removable Needle Systems for Dermal and Transdermal Cryogenic Remodeling," the entire content of which is incorporated herein by reference. Multiple needle arrays may also be arrayed in alternative configurations such as a triangular or square array.

Arrays may be designed to treat a particular region of tissue, or to provide a uniform treatment within a particular region, or both. In some embodiments needle 26 may be releasably coupled with body 16 so that it may be replaced after use with a sharper needle (as indicated by the dotted line) or with a needle having a different configuration. In exemplary embodiments, the needle may be threaded into the body, press fit into an aperture in the body or have a quick disconnect such as a detent mechanism for engaging the needle with the body. A quick disconnect with a check valve may be advantageous since it may permit decoupling of the needle from the body at any time without excessive coolant discharge. This can be a useful safety feature in the event that the device fails in operation (e.g. valve failure), allowing an operator to disengage the needle and device from a patient's tissue without exposing the patient to coolant as the system depressurizes. This feature may also be advantageous because it allows an operator to easily exchange a dull needle with a sharp needle in the middle of a treatment. One of skill in the art will appreciate that other coupling mechanisms may be used.

Addressing some of the components within housing 16, the exemplary cooling fluid supply 18 may comprise a canister, sometimes referred to herein as a cartridge, containing a liquid under pressure, with the liquid preferably having a boiling temperature of less than 37° C. at one atmosphere of pressure. When the fluid is thermally coupled to the tissue-penetrating probe 26, and the probe is positioned within the patient so that an outer surface of the probe is adjacent to a target tissue, the heat from the target tissue evaporates at least a portion of the liquid and the enthalpy of vaporization cools the target tissue. A supply valve 32 may be disposed along the cooling fluid flow path between canister 18 and probe 26, or along the cooling fluid path after the probe so as to limit coolant flow thereby regulating the temperature, treatment time, rate of temperature change, or other cooling characteristics. The valve will often be powered electrically via power source 20, per the direction of processor 22, but may at least in part be manually powered. The exemplary power source 20 comprises a rechargeable or single-use battery. Additional details about valve 32 are disclosed below and further disclosure on the power source 20 may be found in commonly assigned Int'l Pub. No. WO 2010/075438 entitled "Integrated Cryosurgical Probe Package with Fluid Reservoir and Limited Electrical Power Source," the entire contents of which are incorporated herein by reference.

The exemplary cooling fluid supply 18 may comprise a single-use canister. Advantageously, the canister and cooling fluid therein may be stored and/or used at (or even above) room temperature. The canister may have a frangible seal or may be refillable, with the exemplary canister containing liquid nitrous oxide, $N_2O$. A variety of alternative cooling fluids might also be used, with exemplary cooling fluids including fluorocarbon refrigerants and/or carbon dioxide. The quantity of cooling fluid contained by canister 18 will typically be sufficient to treat at least a significant region of a patient, but will often be less than sufficient to treat two or more patients. An exemplary liquid $N_2O$ canister might contain, for example, a quantity in a range from about 1 gram to about 40 grams of liquid, more preferably from about 1 gram to about 35 grams of liquid, and even more preferably from about 7 grams to about 30 grams of liquid.

Processor 22 will typically comprise a programmable electronic microprocessor embodying machine readable computer code or programming instructions for implementing one or more of the treatment methods described herein. The microprocessor will typically include or be coupled to a memory (such as a non-volatile memory, a flash memory, a read-only memory ("ROM"), a random access memory ("RAM"), or the like) storing the computer code and data to be used thereby, and/or a recording media (including a magnetic recording media such as a hard disk, a floppy disk, or the like; or an optical recording media such as a CD or DVD) may be provided. Suitable interface devices (such as digital-to-analog or analog-to-digital converters, or the like) and input/output devices (such as USB or serial I/O ports, wireless communication cards, graphical display cards, and the like) may also be provided. A wide variety of commercially available or specialized processor structures may be used in different embodiments, and suitable processors may make use of a wide variety of combinations of hardware and/or hardware/software combinations. For example, processor 22 may be integrated on a single processor board and may run a single program or may make use of a plurality of boards running a number of different program modules in a wide variety of alternative distributed data processing or code architectures.

Figure 2A:
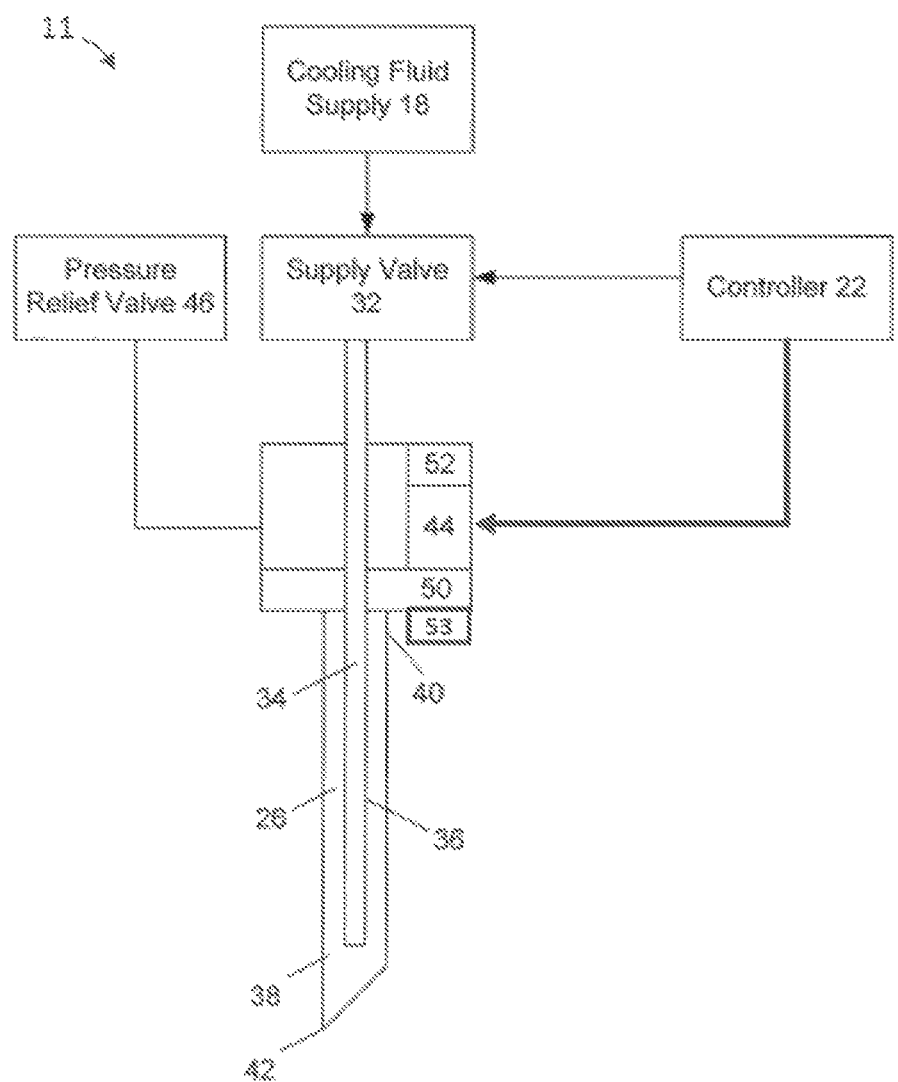
FIG. 2A schematically illustrates exemplary components that may be included in the treatment system.

Referring now to FIG. 2A, schematic 11 shows a simplified diagram of cryogenic cooling fluid flow and control. The flow of cryogenic cooling fluid from fluid supply 18 may be controlled by a supply valve 32. Supply valve 32 may comprise an electrically actuated solenoid valve, a motor actuated valve or the like operating in response to control signals from controller 22, and/or may comprise a manual valve. Exemplary supply valves may comprise structures suitable for on/off valve operation, and may provide venting of the fluid source and/or the cooling fluid path downstream of the valve when cooling flow is halted so as to limit residual cryogenic fluid vaporization and cooling. Additionally, the valve may be actuated by the controller in order to modulate coolant flow to provide high rates of cooling in some instances where it is desirable to promote necrosis of tissue such as in malignant lesions and the like or slow cooling which promotes ice formation between cells rather than within cells when necrosis is not desired. More complex flow modulating valve structures might also be used in other embodiments. For example, other applicable valve embodiments are disclosed in previously incorporated U.S. Pat. No. 8,409,185.

Still referring to FIG. 2A, an optional heater (not illustrated) may be used to heat cooling fluid supply 18 so that heated cooling fluid flows through valve 32 and through a lumen 34 of a cooling fluid supply tube 36. In some embodiments a safety mechanism can be included so that the cooling supply is not overheated. Examples of such embodiments are disclosed in commonly assigned International Publication No. WO 2010075438, the entirety of which is incorporated by reference herein.

Supply tube 36 is, at least in part, disposed within a lumen 38 of needle 26, with the supply tube extending distally from a proximal end 40 of the needle toward a distal end 42. The exemplary supply tube 36 comprises a fused silica tubular structure (not illustrated) having a polymer coating and extending in cantilever into the needle lumen 38. Supply tube 36 may have an inner lumen with an effective inner diameter of less than about 200 µm, the inner diameter often being less than about 100 µm, and typically being less than about 40 µm. Exemplary embodiments of supply tube 36 have inner lumens of between about 15 and 50 µm, such as about 30 µm. An outer diameter or size of supply tube 36 will typically be less than about 1000 µm, often being less than about 800 µm, with exemplary embodiments being between about 60 and 150 µm, such as about 90 µm or 105 µm. The tolerance of the inner lumen diameter of supply tubing 36 will preferably be relatively tight, typically being about +/−10 µm or tighter, often being +/−5 µm or tighter, and ideally being +/−3 µm or tighter, as the small diameter supply tube may provide the majority of (or even substantially all of) the metering of the cooling fluid flow into needle 26. Additional details on various aspects of needle 26 along with alternative embodiments and principles of operation are disclosed in greater detail in U.S. Pat. No. 9,254,162 entitled "Dermal and Transdermal Cryogenic Microprobe Systems and Methods," the entire contents of which are incorporated herein by reference. Previously incorporated U.S. Pat. No. 8,409,185 also discloses additional details on the needle 26 along with various alternative embodiments and principles of operation.

The cooling fluid injected into lumen 38 of needle 26 will typically comprise liquid, though some gas may also be injected. At least some of the liquid vaporizes within needle 26, and the enthalpy of vaporization cools the needle and also the surrounding tissue engaged by the needle. An optional heater 44 (illustrated in FIG. 1B) may be used to heat the proximal region of the needle in order to prevent unwanted skin damage in this area, as discussed in greater detail below. Controlling a pressure of the gas/liquid mixture within needle 26 substantially controls the temperature within lumen 38, and hence the treatment temperature range of the tissue. A relatively simple mechanical pressure relief valve 46 may be used to control the pressure within the lumen of the needle, with the exemplary valve comprising a valve body such as a ball bearing, urged against a valve seat by a biasing spring. An exemplary relief valve is disclosed in U.S. Provisional Patent Application No. 61/116,050 previously incorporated herein by reference. Thus, the relief valve may allow better temperature control in the needle, minimizing transient temperatures. Further details on exhaust volume are disclosed in previously incorporated U.S. Pat. No. 8,409,185.

The heater 44 may be thermally coupled to a thermally responsive element 50, which is supplied with power by the controller 22 and thermally coupled to a proximal portion of the needle 26. The thermally responsive element 50 can be a block constructed from a material of high thermal conductivity and low heat capacity, such as aluminum. A first temperature sensor 52 (e.g., thermistor, thermocouple) can also be thermally coupled the thermally responsive element 50 and communicatively coupled to the controller 22. A second temperature sensor 53 can also be positioned near the heater 44, for example, such that the first temperature sensor 52 and second temperature sensor 53 are placed in different positions within the thermally responsive element 50. In some embodiments, the second temperature sensor 53 is placed closer to a tissue contacting surface than the first temperature sensor 52 is placed in order to provide comparative data (e.g., temperature differential) between the sensors 52, 53. The controller 22 can be configured to receive temperature information of the thermally responsive element 50 via the temperature sensor 52 in order to provide the heater 44 with enough power to maintain the thermally responsive element 50 at a particular temperature.

The controller 22 can be further configured to monitor power draw from the heater 44 in order to characterize tissue type, perform device diagnostics, and/or provide feedback for a tissue treatment algorithm. This can be advantageous over monitoring temperature alone, since power draw from the heater 44 can vary greatly while temperature of the thermally responsive element 50 remains relatively stable. For example, during treatment of target tissue, maintaining the thermally responsive element 50 at 40° C. during a cooling cycle may take 1.0 W initially (for a needle <10 mm in length) and is normally expected to climb to 1.5 W after 20 seconds, due to the needle 26 drawing in surrounding heat. An indication that the heater is drawing 2.0 W after 20 seconds to maintain 40° C. can indicate that an aspect of the system 10 is malfunctioning and/or that the needle 26 is incorrectly positioned. Correlations with power draw and correlated device and/or tissue conditions can be determined experimentally to determine acceptable treatment power ranges.

In some embodiments, it may be preferable to limit frozen tissue that is not at the treatment temperature, i.e., to limit the size of a formed cooling zone within tissue. Such cooling zones may be associated with a particular physical reaction, such as the formation of an ice-ball, or with a particular temperature profile or temperature volume gradient required to therapeutically affect the tissue therein. To achieve this, metering coolant flow could maintain a large thermal gradient at its outside edges. This may be particularly advantageous in applications for creating an array of connected cooling zones (i.e., fence) in a treatment zone, as time would be provided for the treatment zone to fully develop within the fenced in portion of the tissue, while the outer boundaries maintained a relatively large thermal gradient due to the repeated application and removal of refrigeration power. This could provide a mechanism within the body of tissue to thermally regulate the treatment zone and could provide increased ability to modulate the treatment zone at a prescribed distance from the surface of the skin. A related treatment algorithm could be predefined, or it could be in response to feedback from the tissue.

Such feedback could be temperature measurements from the needle 26, or the temperature of the surface of the skin could be measured. However, in many cases monitoring temperature at the needle 26 is impractical due to size constraints. To overcome this, operating performance of the sensorless needle 26 can be interpolated by measuring characteristics of thermally coupled elements, such as the thermally responsive element 50.

Additional methods of monitoring cooling and maintaining an unfrozen portion of the needle include the addition of a heating element and/or monitoring element into the needle itself. This could consist of a small thermistor or thermocouple, and a wire that could provide resistive heat. Other power sources could also be applied such as infrared light, radiofrequency heat, and ultrasound. These systems could also be applied together dependent upon the control of the treatment zone desired.

Alternative methods to inhibit excessively low transient temperatures at the beginning of a refrigeration cycle might be employed instead of or together with the limiting of the exhaust volume. For example, the supply valve 32 might be cycled on and off, typically by controller 22, with a timing sequence that would limit the cooling fluid flowing so that only vaporized gas reached the needle lumen 38 (or a sufficiently limited amount of liquid to avoid excessive dropping of the needle lumen temperature). This cycling might be ended once the exhaust volume pressure was sufficient so that the refrigeration temperature would be within desired limits during steady state flow. Analytical models that may be used to estimate cooling flows are described in greater detail in previously incorporated U.S. Pat. No. 9,254,162.

FIG. 2B shows a cross-section of the housing 16. This embodiment of the housing 16 may be powered by an external source, hence the attached cable, but could alternatively include a portable power source. As shown, the housing includes a cartridge holder 50. The cartridge holder 50 includes a cartridge receiver 52, which may be configured to hold a pressured refrigerant cartridge 18. The cartridge receiver 52 includes an elongated cylindrical passage 54, which is dimensioned to hold a commercially available cooling fluid cartridge 18. A distal portion of the cartridge receiver 52 includes a filter device 56, which has an elongated conical shape. In some embodiments, the cartridge holder 50 may be largely integrated into the housing 16 as shown, however, in alternative embodiments, the cartridge holder 50 is a wholly separate assembly, which may be pre-provided with a coolant fluid source 18.

The filter device 56 may fluidly couple the coolant fluid source (cartridge) 18 at a proximal end to the valve 32 at a distal end. The filter device 56 may include at least one particulate filter 58. In the shown embodiment, a particulate filter 58 at each proximal and distal end of the filter device 56 may be included. The particulate filter 58 can be configured to prevent particles of a certain size from passing through. For example, the particulate filter 58 can be constructed as a microscreen having a plurality of passages less than 2 microns in width, and thus particles greater than 2 microns would not be able to pass.

The filter device 56 also includes a molecular filter 60 that is configured to capture fluid impurities. In some embodiments, the molecular filter 60 is a plurality of filter media (e.g., pellets, powder, particles) configured to trap molecules of a certain size. For example, the filter media can comprise molecular sieves having pores ranging from 1-20 Å. In another example, the pores have an average size of 5 Å. The molecular filter 60 can have two modalities. In a first mode, the molecular filter 60 will filter fluid impurities received from the cartridge 18. However, in another mode, the molecular filter 60 can capture impurities within the valve 32 and fluid supply tube 36 when the system 10 is not in use, i.e., when the cartridge 18 is not fluidly connected to the valve 32.

Alternatively, the filter device 56 can be constructed primarily from ePTFE (such as a GORE material), sintered polyethylene (such as made by POREX), or metal mesh. The pore size and filter thickness can be optimized to minimize pressure drop while capturing the majority of contaminants. These various materials can be treated to make it hydrophobic (e.g., by a plasma treatment) and/or oleophobic so as to repel water or hydrocarbon contaminants.

It has been found that in some instances fluid impurities may leach out from various aspects of the system 10. These impurities can include trapped moisture in the form of water molecules and chemical gasses. The presence of these impurities is believed to hamper cooling performance of the system 10. The filter device 56 can act as a desiccant that attracts and traps moisture within the system 10, as well as chemicals out gassed from various aspects of the system 10. Alternately the various aspects of the system 10 can be coated or plated with impermeable materials such as a metal.

Figure 2C:
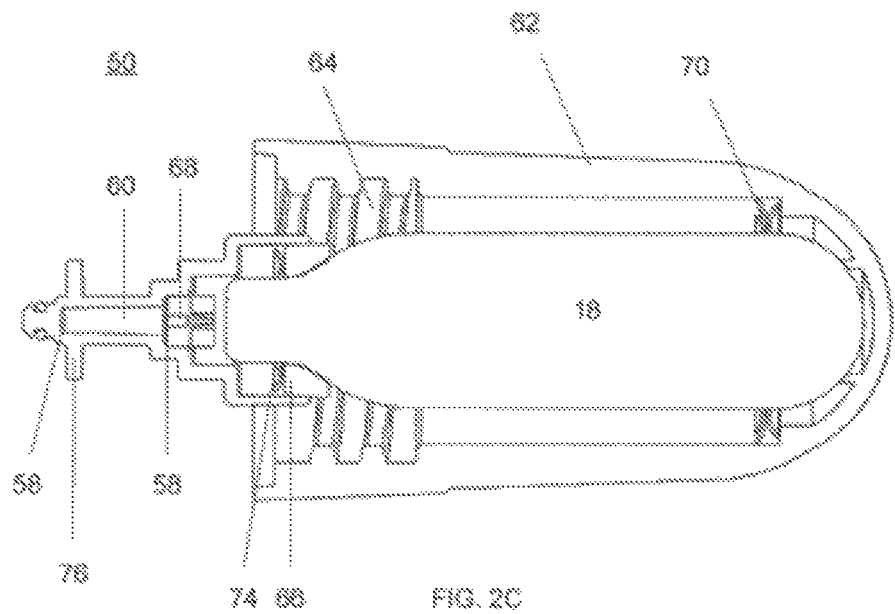
FIGS. 2C and 2D are cross-sectional views showing exemplary operational configurations of a portion of the system of FIG. 2B.
Figure 2D:
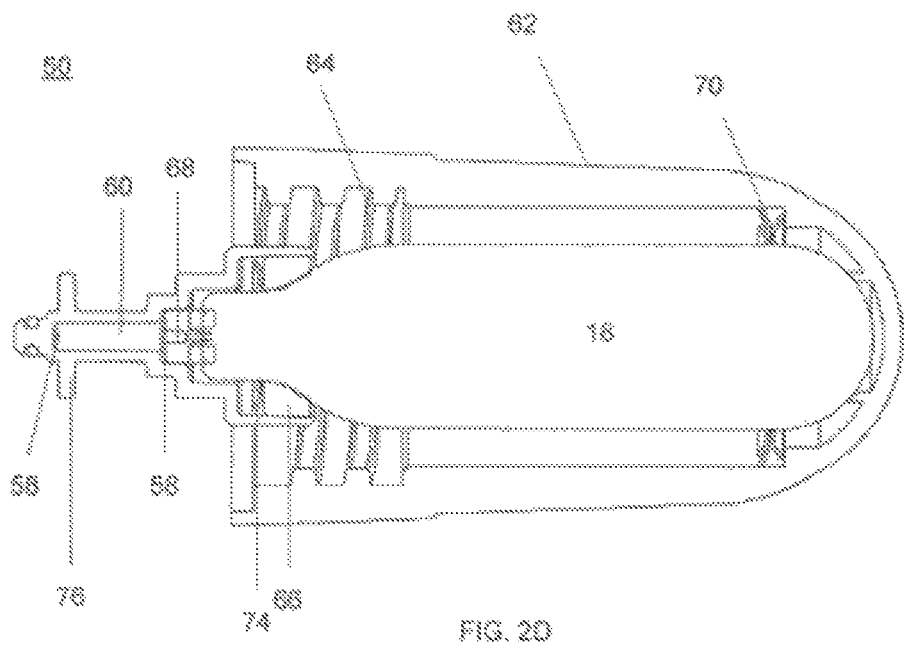

As shown in FIG. 2B and in more detail in FIG. 2C and FIG. 2D, the cartridge 18 can be held by the cartridge receiver 52 such that the cartridge 18 remains intact and unpunctured. In this inactive mode, the cartridge may not be fluidly connected to the valve 32. A removable cartridge cover 62 can be attached to the cartridge receiver 52 such that the inactive mode is maintained while the cartridge is held by the system 10.

In use, the cartridge cover 62 can be removed and supplied with a cartridge containing a cooling fluid. The cartridge cover 62 can then be reattached to the cartridge receiver 52 by turning the cartridge cover 62 until female threads 64 of the cartridge cover 62 engage with male threads of the cartridge receiver 52. The cartridge cover 62 can be turned until resilient force is felt from an elastic seal 66, as shown in FIG. 2C. To place the system 10 into use, the cartridge cover 62 can be further turned until the distal tip of the cartridge 18 is punctured by a puncture pin connector 68, as shown in FIG. 2D. Once the cartridge 18 is punctured, cooling fluid may escape the cartridge by flowing through the filter device 56, where the impurities within the cooling fluid may be captured. The purified cooling fluid then passes to the valve 32, and onto the coolant supply tube 36 to cool the probe 26. In some embodiments the filter device, or portions thereof, may be replaceable.

In some embodiments, the puncture pin connector 68 can have a two-way valve (e.g., ball/seat and spring) that is closed unless connected to the cartridge. Alternately, pressure can be used to open the valve. The valve closes when the cartridge is removed. In some embodiments, there may be a relief valve piloted by a spring which is balanced by high-pressure nitrous when the cartridge is installed and the system is pressurized, but allows the high-pressure cryogen to vent when the cryogen is removed. In addition, the design can include a vent port that vents cold cryogen away from the cartridge port. Cold venting cryogen locally can cause condensation in the form of liquid water to form from the surrounding environment. Liquid water or water vapor entering the system can hamper the cryogenic performance. Further, fluid carrying portions of the cartridge receiver 52 can be treated (e.g., plasma treatment) to become hydrophobic and/or oleophobic so as to repel water or hydrocarbon contaminants.

Figure 3A:
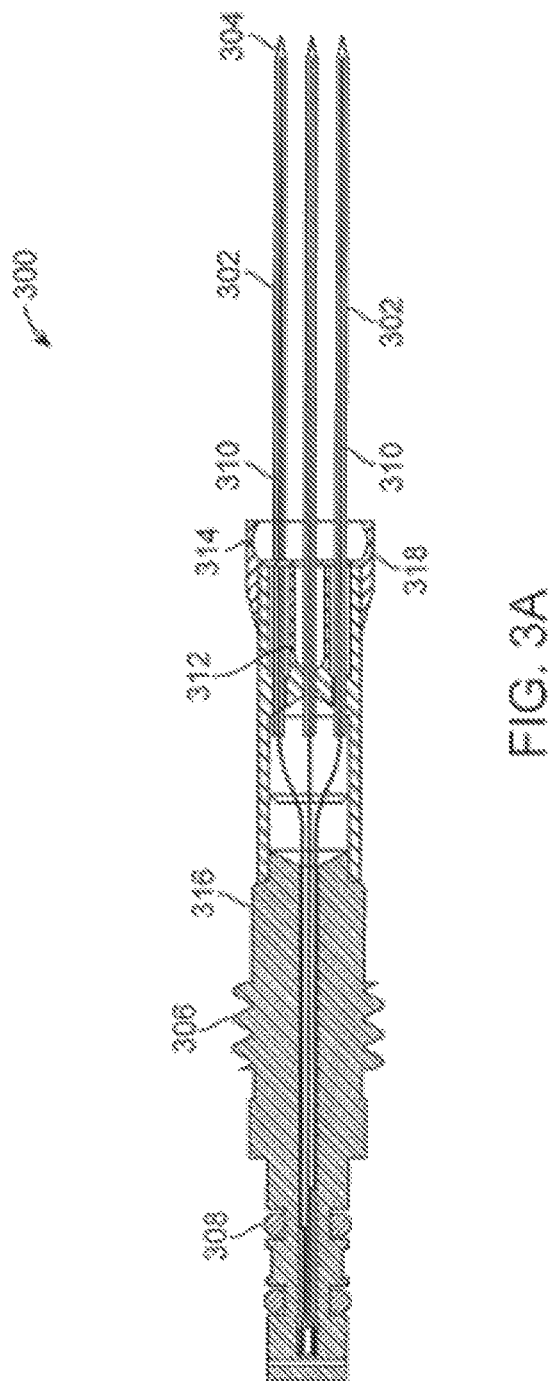
Figure 3B:
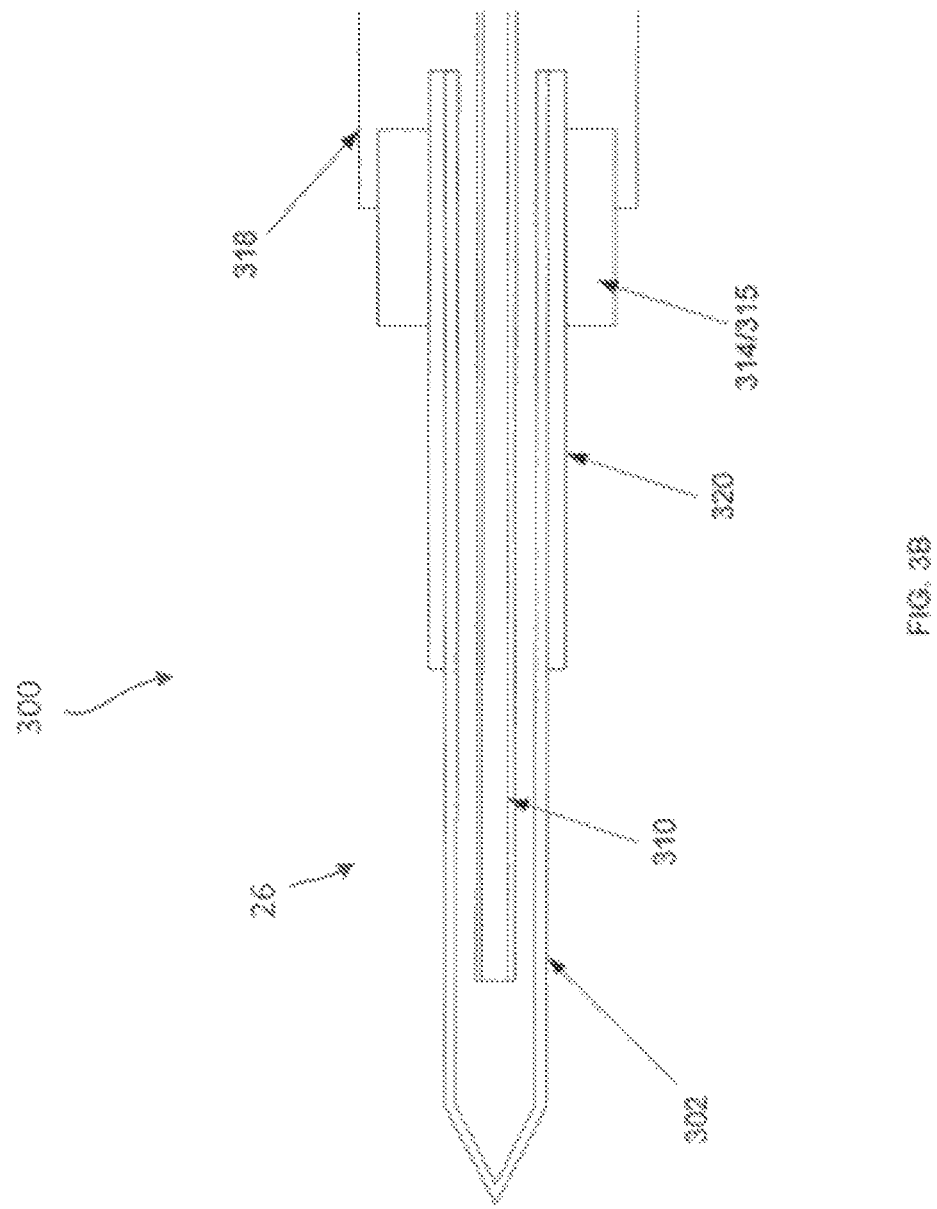

Turning now to FIG. 3A and FIG. 3B, an exemplary embodiment of probe 300 having multiple needles 302 is described. In FIG. 3A, probe housing 316 includes threads 306 that allow the probe to be threadably engaged with the housing 16 of a cryogenic device. 0-rings 308 fluidly seal the probe housing 316 with the device housing 16 and prevent coolant from leaking around the interface between the two components. Probe 300 includes an array of three distally extending needle shafts 302, each having a sharpened, tissue penetrating tip 304. Using three linearly arranged needles allows a greater area of tissue to be treated as compared with a single needle. In use, coolant flows through lumens 310 into the needle shafts 302 thereby cooling the needle shafts 302. Ideally, only the distal portion of the needle shaft 302 would be cooled so that only the target tissue receives the cryogenic treatment. However, as the cooling fluid flows through the probe 300, probe temperature decreases proximally along the length of the needle shafts 302 towards the probe hub 318. The proximal portion of needle shaft 302 and the probe hub 318 contact skin and may become very cold (e.g. −20° C. to −25° C.) and this can damage the skin in the form of blistering or loss of skin pigmentation. Therefore it would be desirable to ensure that the proximal portion of needle shaft 302 and hub 318 remains warmer than the distal portion of needle shaft 302. A proposed solution to this challenge is to include a heater element 314 that can heat the proximal portion of needle shaft 302 and an optional temperature sensor 312 to monitor temperature in this region. To further this, a proximal portion of the needle shaft 302 can be coated with a highly thermally conductive material, e.g., gold, that is conductively coupled to both the needle shaft 302 and heater element 314. Details of this construction are disclosed below.

In the exemplary embodiment of FIG. 3A, resistive heater element 314 is disposed near the needle hub 318 and near a proximal region of needle shaft 302. The resistance of the heater element is preferably 1Ω to 1K Ω, and more preferably from 5Ω to 50Ω. Additionally, a temperature sensor 312 such as a thermistor or thermocouple is also disposed in the same vicinity. Thus, during a treatment as the needles cool down, the heater 314 may be turned on in order to heat the hub 318 and proximal region of needle shaft 302, thereby preventing this portion of the device from cooling down as much as the remainder of the needle shaft 302. The temperature sensor 312 may provide feedback to controller 22 and a feedback loop can be used to control the heater 314. The cooling power of the nitrous oxide may eventually overcome the effects of the heater, therefore the microprocessor may also be programmed with a warning light and/or an automatic shutoff time to stop the cooling treatment before skin damage occurs. An added benefit of using such a heater element is the fact that the heat helps to moderate the flow of cooling fluid into the needle shaft 302 helping to provide more uniform coolant mass flow to the needles shaft 302 with more uniform cooling resulting.

The embodiment of FIG. 3A illustrates a heater fixed to the probe hub. In other embodiments, the heater may float, thereby ensuring proper skin contact and proper heat transfer to the skin. Examples of floating heaters are disclosed in commonly assigned Int'l Pub. No. WO 2010/075448 entitled "Skin Protection for Subdermal Cryogenic Remodeling for Cosmetic and Other Treatments," the entirety of which is incorporated by reference herein.

In this exemplary embodiment, three needles are illustrated. One of skill in the art will appreciate that a single needle may be used, as well as two, four, five, six, or more needles may be used. When a plurality of needles are used, they may be arranged in any number of patterns. For example, a single linear array may be used, or a two dimensional or three dimensional array may be used. Examples of two dimensional arrays include any number of rows and columns of needles (e.g. a rectangular array, a square array, elliptical, circular, triangular, etc.), and examples of three dimensional arrays include those where the needle tips are at different distances from the probe hub, such as in an inverted pyramid shape.

FIG. 3B illustrates a cross-section of the needle shaft 302 of needle probe 300. The needle shaft can be conductively coupled (e.g., welded, conductively bonded, press fit) to a conductive heater 314 to enable heat transfer therebetween. The needle shaft 302 is generally a small (e.g., 20-30 gauge) closed tip hollow needle, which can be between about 0.2 mm and 15 cm, preferably having a length from about 0.3 cm to about 3 cm. The conductive heater element 314 can be housed within a conductive block 315 of high thermally conductive material, such as aluminum and include an electrically insulated coating, such as Type III anodized coating to electrically insulate it without diminishing its heat transfer properties. The conductive block 315 can be heated by a resister or other heating element (e.g. cartridge heater, nichrome wire, etc.) bonded thereto with a heat conductive adhesive, such as epoxy. A thermistor can be coupled to the conductive block 315 with heat conductive epoxy allows temperature monitoring. Other temperature sensors may also be used, such as a thermocouple.

A cladding 320 of conductive material is directly conductively coupled to the proximal portion of the shaft of the needle 302, which can be stainless steel. In some embodiments, the cladding 320 is a layer of gold, or alloys thereof, coated on the exterior of the proximal portion of the needle shaft 302. In some embodiments, the exposed length of cladding 320 on the proximal portion of the needle is 2-100 mm. In some embodiments, the cladding 320 can be of a thickness such that the clad portion has a diameter ranging from 0.017-0.020 in., and in some embodiments 0.0182 in. Accordingly, the cladding 320 can be conductively coupled to the material of the needle 302, which can be less conductive, than the cladding 320. The cladding 320 may modify the lateral force required to deflect or bend the needle 26. Cladding 320 may be used to provide a stiffer needle shaft along the proximal end in order to more easily transfer force to the leading tip during placement and allow the distal portion of the needle to deflect more easily when it is dissecting a tissue interface within the body. The stiffness of needle 26 can vary from one end to the other end by other means such as material selection, metal tempering, variation of the inner diameter of the needle 26, or segments of needle shaft joined together end-to-end to form one contiguous needle 26. In some embodiments, increasing the stiffness of the distal portion of the needle 26 can be used to flex the proximal portion of the needle to access difficult treatment sites as in the case of upper limb spasticity where bending of the needle outside the body may be used to access a target peripheral nerve along the desired tissue plane.

In some embodiments, the cladding 320 can include sub-coatings (e.g., nickel) that promote adhesion of an outer coating that would otherwise not bond well to the needle shaft 302. Other highly conductive materials can be used as well, such as copper, silver, aluminum, and alloys thereof. In some embodiments, a protective polymer or metal coating can cover the cladding to promote biocompatibility of an otherwise non-biocompatible but highly conductive cladding material. Such a biocompatible coating however, would be applied to not disrupt conductivity between the conductive block 315. In some embodiments, an insulating layer, such as a ceramic material, is coated over the cladding 320, which remains conductively coupled to the needle shaft 302.

In use, the cladding 320 can transfer heat to the proximal portion of the needle 302 to prevent directly surrounding tissue from dropping to cryogenic temperatures. Protection can be derived from heating the non-targeting tissue during a cooling procedure, and in some embodiments before the procedure as well. The mechanism of protection may be providing heat to pressurized cryogenic cooling fluid passing within the proximal portion of the needle to affect complete vaporization of the fluid. Thus, the non-target tissue in contact with the proximal portion of the needle shaft 302 does not need to supply heat, as opposed to target tissue in contact with the distal region of the needle shaft 302. To help further this effect, in some embodiments the cladding 320 is coating within the interior of the distal portion of the needle, with or without an exterior cladding. To additionally help further this effect, in some embodiments, the distal portion of the needle can be thermally isolated from the proximal portion by a junction, such as a ceramic junction. While in some further embodiments, the entirety of the proximal portion is constructed from a more conductive material than the distal portion.

In use, it has been determined experimentally that the cladding 320 can help limit formation of a cooling zone to the distal portion of the needle shaft 302, which tends to demarcate at a distal end of the cladding 320. Accordingly, cooling zones are formed only about the distal portions of the needles. Thus, non-target tissue in direct contact with proximal needle shafts remain protected from effects of cryogenic temperatures. Such effects can include discoloration and blistering of the skin. Such cooling zones may be associated with a particular physical reaction, such as the formation of an ice-ball, or with a particular temperature required to therapeutically affect the tissue therein.

Standard stainless steel needles and gold clad steel needles were tested in porcine muscle and fat. Temperatures were recorded measured 2 mm from the proximal end of the needle shafts, about where the cladding distally terminates, and at the distal tip of the needles. Temperatures for clad needles were dramatically warmer at the 2 mm point versus the unclad needles, and did not drop below 4° C. The 2 mm points of the standard stainless steel needles almost equalize in temperature with the distal tip at temperatures below 0° C.

FIGS. 3C and 3D illustrates a detachable probe tip 322 having a hub connector 324 and an elongated probe 326. The probe tip 322 shares much of its construction with probe 300. However, the elongated probe 326 features a blunt tip 328 that is adapted for blunt dissection of tissue. The blunt tip 328 can feature a full radius tip, less than a full radius tip, or conical tip. In some embodiments, a dulled or truncated needle is used. The elongated probe 326 can be 20 gauge or smaller in diameter, and in some embodiments range in size from 25-30 gauge. As with the embodiments described above, an internal supply tube 330 extends in cantilever. However, the exit of the supply tube 330 can be disposed at positions within the elongated probe 326 other than proximate the blunt tip 328. Further, the supply tube 330 can be adapted to create an elongated zone of cooling, e.g., by having multiple exit points for cryofluid to exit from.

The elongated probe 326 and supply tube 330 may be configured to resiliently bend in use, throughout their length at angles approaching 120°, with a 5-10 mm bend radius. This may be very challenging considering the small sizes of the elongated probe 326 and supply tube 330, and also considering that the supply tube 330 is often constructed from fused silica. Accordingly, the elongated probe 326 can be constructed from a resilient material, such as stainless steel, and of a particular diameter and wall thickness [0.004 to 1.0 mm], such that the elongated probe in combination with the supply tube 330 is not overly resilient so as to overtly resist manipulation, but sufficiently strong so as to prevent kinking that can result in coolant escaping. For example, the elongated probe can be 15 gauge or smaller in diameter, even ranging from 20-30 gauge in diameter. The elongated probe can have a very disparate length to diameter ratio, for example, the elongated probe can be greater than 30 mm in length, and in some cases range from 30-100 mm in length. To further the aforementioned goals, the supply tube 330 can include a polymer coating 332, such as a polyimide coating that terminates approximately halfway down its length, to resist kinking and aid in resiliency. The polymer coating 332 can be a secondary coating over a primary polyimide coating that extends fully along the supply tube. However, it should be understood that the coating is not limited to polyimide, and other suitable materials can be used. In some embodiments, the flexibility of the elongated probe 326 will vary from the proximal end to the distal end. For example, by creating certain portions that have more or less flexibility than others. This may be done, for example, by modifying wall thickness, adding material (such as the cladding discussed above), and/or heat treating certain portions of the elongated probe 326 and/or supply tube 330. For example, decreasing the flexibility of elongated probe 326 along the proximal end can improve the transfer of force from the hand piece to the elongated probe end for better feel and easier tip placement for treatment. The elongated probe and supply line 330 are may be configured to resiliently bend in use to different degrees along the length at angles approaching 120°, with a varying bend radius as small as 5 mm. In some embodiments, the elongated probe 326 will have external markings along the needle shaft indicating the length of needle inserted into the tissue.

Figure 3E:
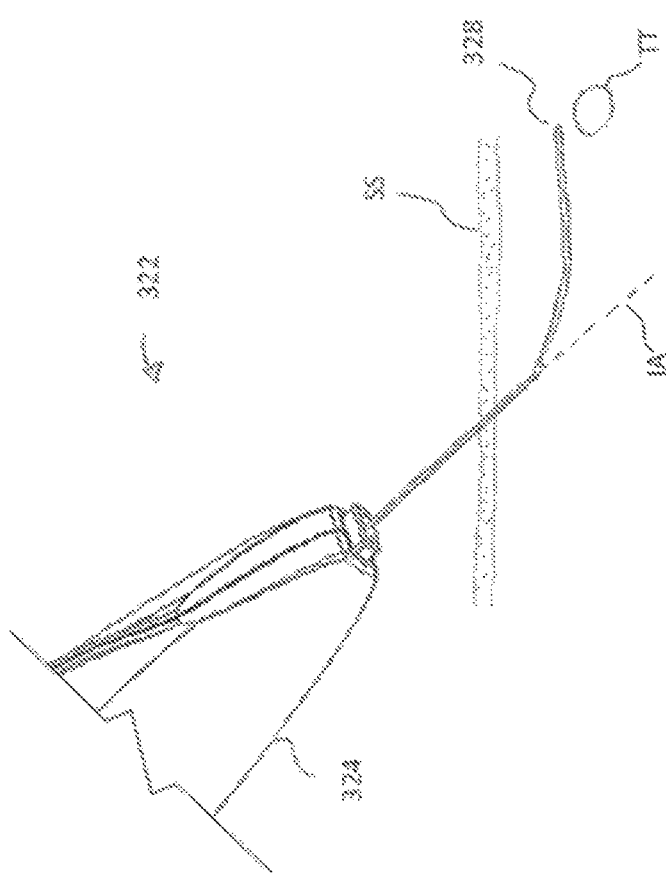

FIG. 3E illustrates an exemplary detachable probe tip 322 inserted through skin surface SS. As illustrated, the probe tip 322 is inserted along an insertion axis IA through the skin surface SS. Thereafter, the needle may be bent away from the insertion axis IA and advanced toward a target tissue TT in order to position blunt tip 328 adjacent to the target tissue TT. In some embodiments, the target tissue may be the infrapatellar branch of the saphenous nerve. In other embodiments the target tissue may be one or more branches of the anterior femoral cutaneous nerve or the lateral femoral cutaneous nerve.

In some embodiments, the probe tip 322 does not include a heating element, such as the heater described with reference to probe 300, since the effective treating portion of the elongated probe 326 (i.e., the area of the elongated probe where a cooling zone emanates from) is well laterally displaced from the hub connector 324 and elongated probe proximal junction. Embodiments of the supply tube are further described below and within commonly assigned U.S. Pub. No. 2012/0089211, which is incorporated by reference.

Figure 4A:
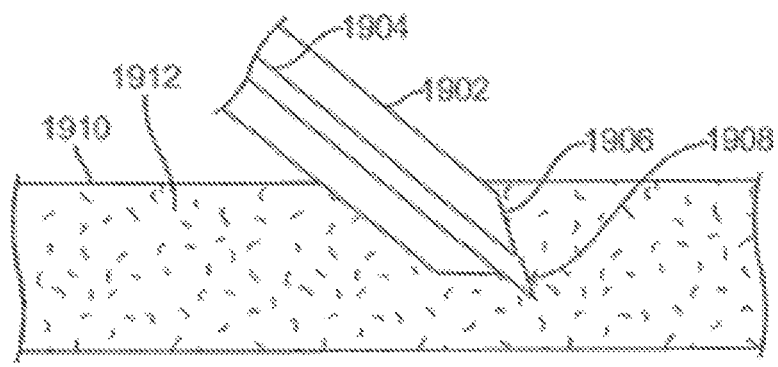
FIGS. 4A-4C illustrate an exemplary method of introducing a cryogenic probe to a treatment area, according to some embodiments of the invention.
Figure 4B:
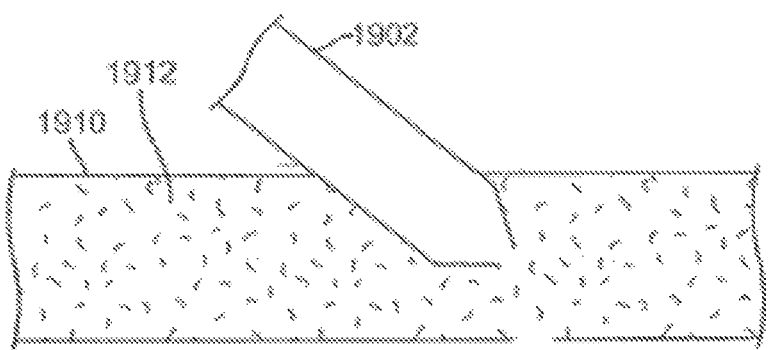
Figure 4C:
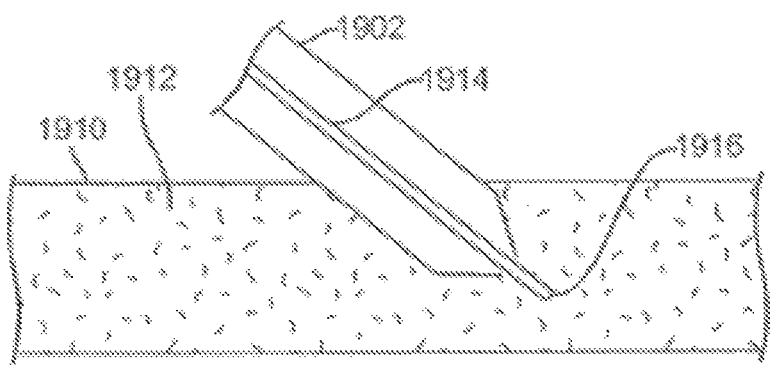

FIGS. 4A-4C illustrate an exemplary method of creating a hole through the skin that allows multiple insertions and positioning of a cryoprobe therethrough. This may be helpful when the needle must be advanced distally past dense scar tissue. In FIG. 4A a cannula or sheath 1902 is disposed over a needle 1904 having a tissue penetrating distal end 1908. The cannula may have a tapered distal portion 1906 to help spread and dilate the skin during insertion. The needle/sheath assembly is then advanced into and pierces the skin 1910 into the desired target tissue 1912. The inner pathway of the cannula or sheath 1902 may be curved to assist in directing the flexible needle 1904, or other probe, into a desired tissue layer coincident with the desired needle path in the tissue. Once the needle/sheath assembly has been advanced to a desired location, the needle 1904 may be proximally retracted and removed from the sheath 1902. The sheath (or introducer) now may be used as an easy way of introducing a cryoprobe through the skin without piercing it, and directing the cryoprobe to the desired target treatment area. FIG. 4B shows the sheath 1902 in position with the needle 1904 removed. FIG. 4C shows insertion of a cryoprobe 1914 into the sheath such that a blunt tip 1916 of the cryoprobe 1914 is adjacent the target treatment tissue. The cryoprobe may then be cooled and the treatment tissue cooled to achieve any of the cosmetic or therapeutic effects discussed above. In this embodiment, the cryoprobe preferably has a blunt tip 1916 in order to minimize tissue trauma. In other embodiments, the tip may be sharp and be adapted to penetrate tissue, or it may be round and spherical. The cryoprobe 1914 may then be at least partially retracted from the sheath 1902 and/or rotated and then re-advanced to the same or different depth and repositioned in sheath 1902 so that the tip engages a different portion of the target treatment tissue without requiring an additional piercing of the skin. The probe angle relative to the tissue may also be adjusted, and the cryoprobe may be advanced and retracted multiple times through the sheath so that the entire target tissue is cryogenically treated.

While the embodiment of FIGS. 4A-4C illustrates a cryoprobe having only a single probe, the cryoprobe may have an array of probes. Any of the cryoprobes described above may be used with an appropriately sized sheath. In some embodiments, the cryoprobe comprises a linear or two dimensional array of probes. Lidocaine or other local anesthetics may be used during insertion of the sheath or cryoprobe in order to minimize patient discomfort. The angle of insertion for the sheath may be anywhere from 0 to 180 degrees relative to the skin surface, and in specific embodiments is 15 to 45 degrees. The sheath may be inserted at any depth, but in specific embodiments of treating lines/wrinkles of the face, the sheath may be inserted to a depth of 1 mm to 10 mm, and more preferably to a depth of 2 mm to 5 mm.

Figure 4D:
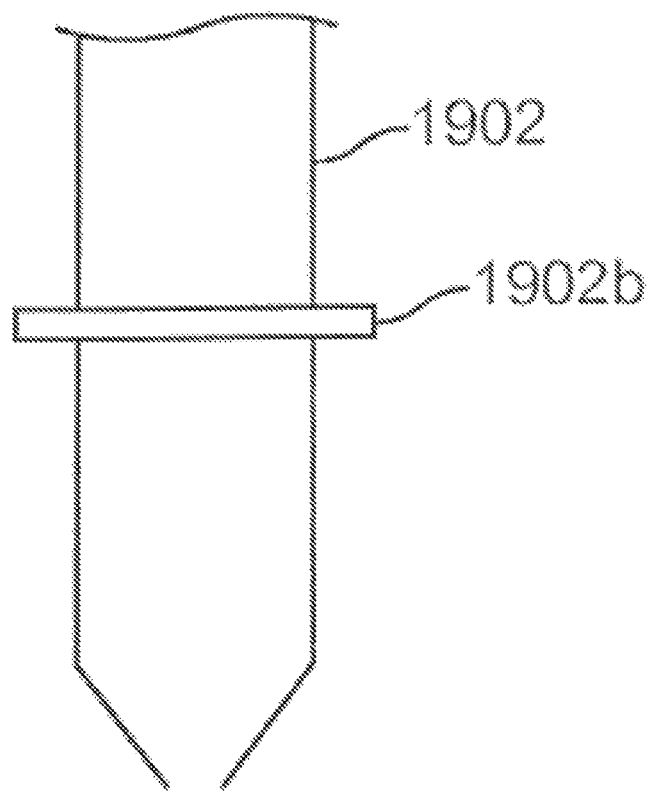
FIG. 4D illustrates an alternative exemplary embodiment of a sheath, according to some embodiments of the invention.

In an alternative embodiment seen in FIG. 4D, the sheath 1902 may include an annular flange 1902b on an outside surface of the sheath in order to serve as a stop so that the sheath is only inserted a preset amount into the tissue. The position of the flange 1902b may be adjustable or fixed. The proximal end of the sheath in this embodiment, or any of the other sheath embodiments may also include a one way valve such as a hemostasis valve to prevent backflow of blood or other fluids that may exit the sheath. The sheath may also insulate a portion of the cryoprobe and prevent or minimize cooling of unwanted regions of tissue.

Figure 5:
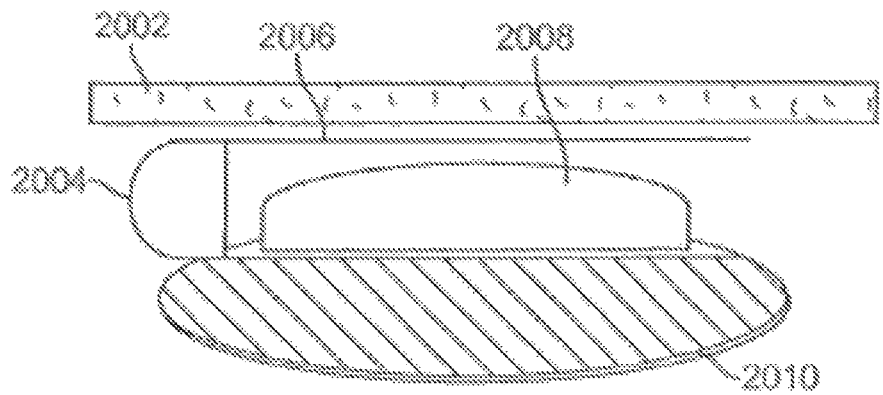
FIG. 5 illustrates an exemplary insulated cryoprobe, according to some embodiments of the invention.

Any of the cryoprobes described above may be used with the sheath embodiment described above (e.g. in FIGS. 3B, 4A-4C). Other cryoprobes may also be used with this sheath embodiment, or they may be used alone, in multi-probe arrays, or combined with other treatments. For example, a portion of the cryoprobe 2006 may be insulated as seen in FIG. 5. Cryoprobe 2006 includes a blunt tip 2004 with an insulated section 2008 of the probe. Thus, when the cryoprobe is disposed in the treatment tissue under the skin 2002 and cooled, the cryoprobe preferentially creates a cooling zone along one side while the other side remains uncooled, or only experiences limited cooling. For example, in FIG. 5, the cooling zone 2010 is limited to a region below the cryoprobe 2006, while the region above the cryoprobe and below the skin 2002 remain unaffected by the cooling.

Figure 6:
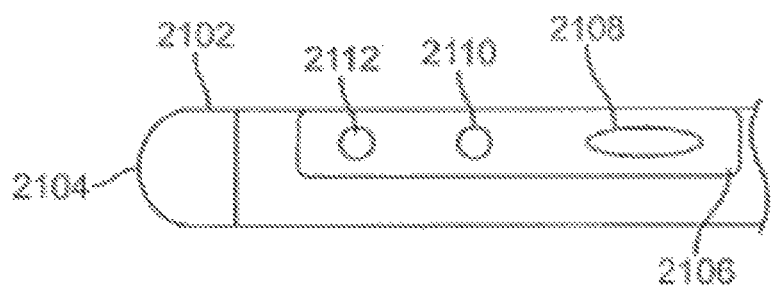
FIGS. 6-9 illustrate exemplary embodiments of cryofluid delivery tubes, according to some embodiments of the invention.
Figure 7:
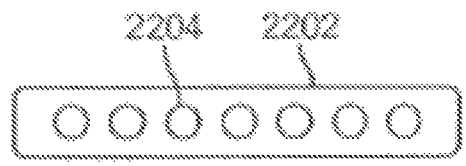
Figure 8:
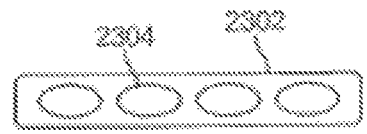
Figure 9:
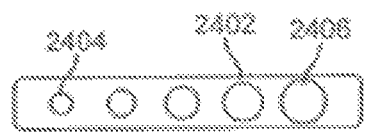

Different zones of cryotherapy may also be created by different geometries of the coolant fluid supply tube that is disposed in the cryoprobe. FIGS. 6-9 illustrate exemplary embodiments of different coolant fluid supply tubes. In FIG. 6 the coolant fluid supply tube 2106 is offset from the central axis of a cryoprobe 2102 having a blunt tip 2104. Additionally, the coolant fluid supply tube 2106 includes several exit ports for the coolant including circular ports 2110, 2112 near the distal end of the coolant fluid supply tube and an elliptical port 2108 proximal of the other ports. These ports may be arranged in varying sizes, and varying geometries in order to control the flow of cryofluid which in turn controls probe cooling of the target tissue. FIG. 7 illustrates an alternative embodiment of a coolant fluid supply tube 2202 having a plurality of circular ports 2204 for controlling cryofluid flow. FIG. 8 illustrates yet another embodiment of a coolant fluid supply tube 2302 having a plurality of elliptical holes 2304, and FIG. 9 shows still another embodiment of a coolant fluid supply tube 2402 having a plurality of ports ranging from smaller diameter circular holes 2404 near the distal end of the supply tube 2402 to larger diameter circular holes 2406 that are more proximally located on the supply tube 2402.

Figure 10:
FIG. 10 illustrates an example of blunt tipped cryoprobe, according to some embodiments of the invention.

As discussed above, it may be preferable to have a blunt tip on the distal end of the cryoprobe in order to minimize tissue trauma. The blunt tip may be formed by rounding off the distal end of the probe, or a bladder or balloon 2506 may be placed on the distal portion of the probe 2504 as seen in FIG. 10. A filling tube or inflation lumen 2502 may be integral with or separate from the cryoprobe 2504, and may be used to deliver fluid to the balloon to fill the balloon 2506 up to form the atraumatic tip.

Figure 11:
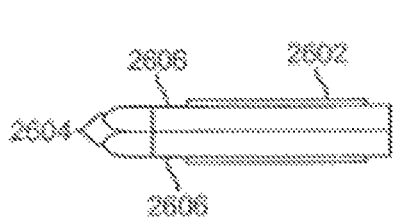
FIGS. 11 and 12 illustrate exemplary actuatable cryoprobes, according to some embodiments of the invention.
Figure 12:
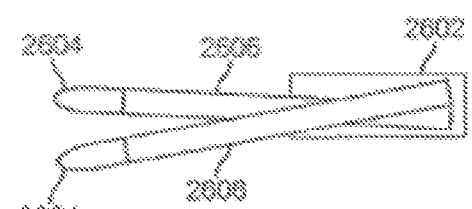

In some instances, it may be desirable to provide expandable cryoprobes that can treat different target tissues or accommodate different anatomies. For example, in FIGS. 11 and 12, a pair of cryoprobes 2606 with blunt tips 2604 may be delivered in parallel with one another and in a low profile through a sheath 2602 to the treatment area. Once delivered, the probes may be actuated to separate the tips 2604 from one another, thereby increasing the cooling zone. After the cryotherapy has been administered, the probes may be collapsed back into their low profile configuration, and retracted from the sheath.

In some embodiments, the probe may have a sharp tissue piercing distal tip, and in other embodiments, the probe may have a blunt tip for minimizing tissue trauma. To navigate through tissue, it may be desirable to have a certain column strength for the probe in order to avoid bending, buckling or splaying, especially when the probe comprises two or more probes in an array. One exemplary embodiment may utilize a variable stiff portion of a sleeve along the probe body to provide additional column strength for pushing the probe through tissue.

Figure 13:
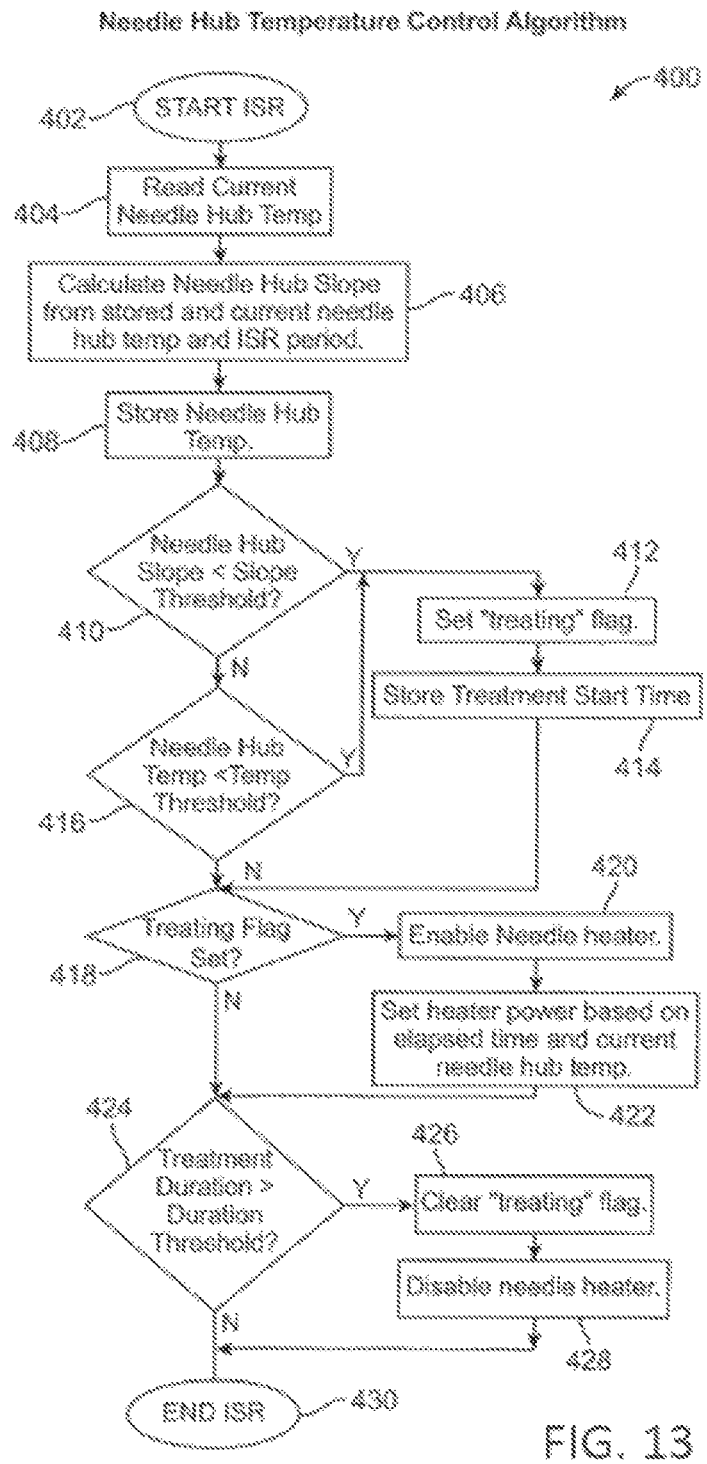
FIG. 13 is a flow chart illustrating an exemplary algorithm for heating the needle probe of FIG. 3A, according to some embodiments of the invention.

An exemplary algorithm 400 for controlling the heater element 314, and thus for transferring heat to the cladding 320, is illustrated in FIG. 13. In FIG. 13, the start of the interrupt service routine (ISR) 402 begins with reading the current needle hub temperature 404 using a temperature sensor such as a thermistor or thermocouple disposed near the needle hub. The time of the measurement is also recorded. This data is fed back to controller 22 where the slope of a line connecting two points is calculated. The first point in the line is defined by the current needle hub temperature and time of its measurement and the second point consists of a previous needle hub temperature measurement and its time of measurement. Once the slope of the needle hub temperature curve has been calculated 406, it is also stored 408 along with the time and temperature data. The needle hub temperature slope is then compared with a slope threshold value 410. If the needle hub temperature slope is less than the threshold value then a treating flag is activated 412 and the treatment start time is noted and stored 414. If the needle hub slope is greater than or equal to the slope threshold value 410, an optional secondary check 416 may be used to verify that cooling has not been initiated. In step 416, absolute needle hub temperature is compared to a temperature threshold. If the hub temperature is less than the temperature threshold, then the treating flag is activated 412 and the treatment start time is recorded 414 as previously described. As an alternative, the shape of the slope could be compared to a norm, and an error flag could be activated for an out of norm condition. Such a condition could indicate the system was not heating or cooling sufficiently. The error flag could trigger an automatic stop to the treatment with an error indicator light. Identifying the potential error condition and possibly stopping the treatment may prevent damage to the proximal tissue in the form of too much heat, or too much cooling to the tissue. The algorithm preferably uses the slope comparison as the trigger to activate the treatment flag because it is more sensitive to cooling conditions when the cryogenic device is being used rather than simply measuring absolute temperature. For example, a needle probe exposed to a cold environment would gradually cool the needle down and this could trigger the heater to turn on even though no cryogenic cooling treatment was being conducted. The slope more accurately captures rapid decreases in needle temperature as are typically seen during cryogenic treatments.

When the treatment flag is activated 418 the needle heater is enabled 420 and heater power may be adjusted based on the elapsed treatment time and current needle hub temperature 422. Thus, if more heat is required, power is increased and if less heat is required, power is decreased. Whether the treatment flag is activated or not, as an additional safety mechanism, treatment duration may be used to control the heater element 424. As mentioned above, eventually, cryogenic cooling of the needle will overcome the effects of the heater element. In that case, it would be desirable to discontinue the cooling treatment so that the proximal region of the probe does not become too cold and cause skin damage. Therefore, treatment duration is compared to a duration threshold value in step 424. If treatment duration exceeds the duration threshold then the treatment flag is cleared or deactivated 426 and the needle heater is deactivated 428. If the duration has not exceeded the duration threshold 424 then the interrupt service routine ends 430. The algorithm then begins again from the start step 402. This process continues as long as the cryogenic device is turned on.

Preferred ranges for the slope threshold value may range from about −5° C. per second to about −90° C. per second and more preferably range from about −30° C. per second to about −57° C. per second. Preferred ranges for the temperature threshold value may range from about 15° C. to about 0° C., and more preferably may range from about 0° C. to about 10° C. Treatment duration threshold may range from about 15 seconds to about 75 seconds.

It should be appreciated that the specific steps illustrated in FIG. 13 provide a particular method of heating a cryogenic probe, according to an embodiment of the present invention. Other sequences of steps may also be performed according to alternative embodiments. For example, alternative embodiments of the present invention may perform the steps outlined above in a different order. Moreover, the individual steps illustrated in FIG. 13 may include multiple sub-steps that may be performed in various sequences as appropriate to the individual step. Furthermore, additional steps may be added or removed depending on the particular applications.

Figure 14:
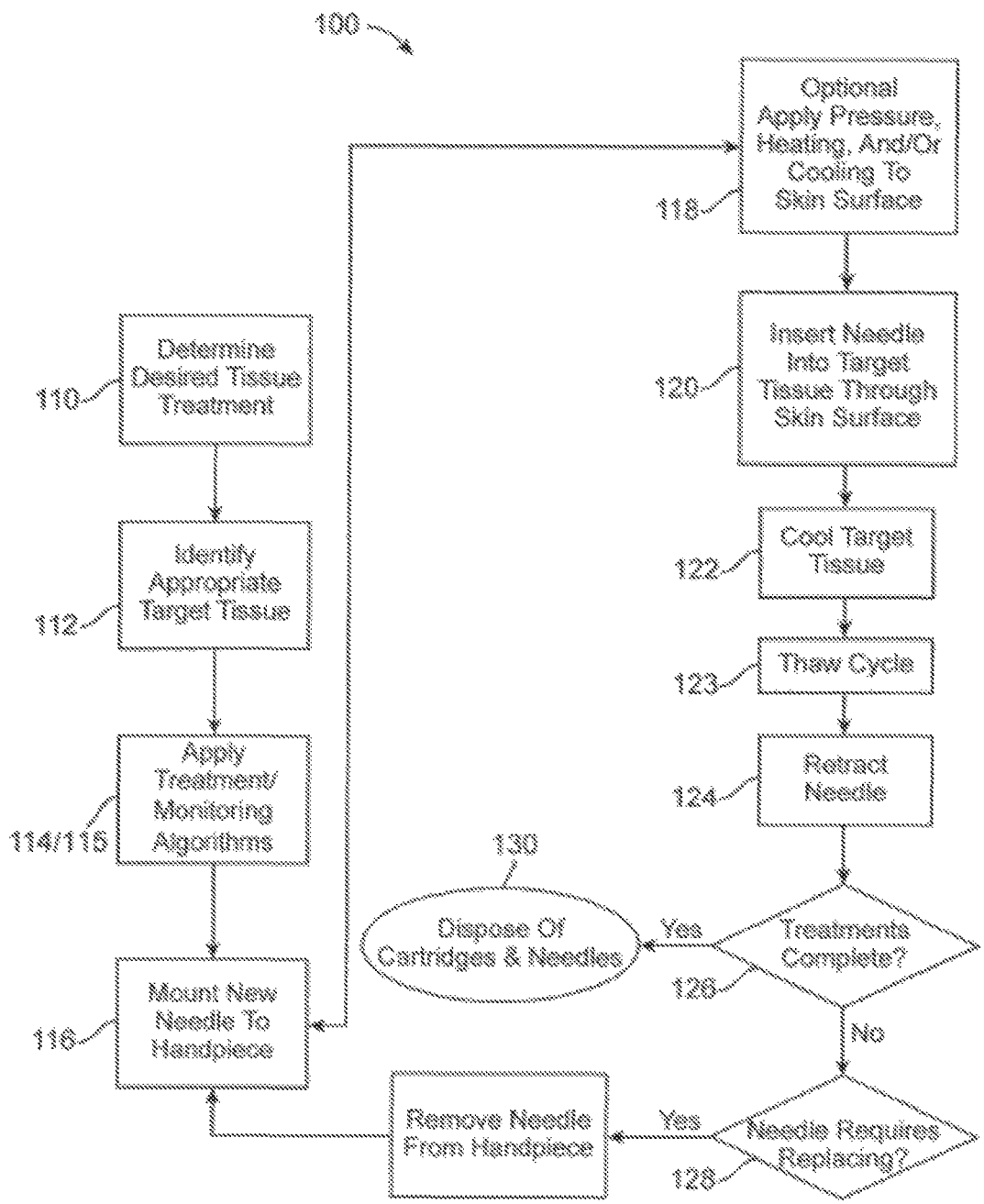
FIG. 14 is a flow chart schematically illustrating an exemplary method for treatment using the disposable cryogenic probe and system of FIGS. 1A and 1B, according to some embodiments of the invention.

The heating algorithm may be combined with a method for treating a patient. Referring now to FIG. 14, a method 100 facilitates treating a patient using a cryogenic cooling system having a reusable or disposable handpiece either of which that can be self-contained or externally powered with replaceable needles such as those of FIG. 1B and a limited capacity battery or metered electrical supply. Method 100 generally begins with a determination 110 of the desired tissue therapy and results, such as the inhibition of pain from a particular site. Appropriate target tissues for treatment are identified 112 (a tissue that transmits the pain signal), allowing a target treatment depth, target treatment temperature profile, or the like to be determined. Step 112 may include performing a tissue characterization and/or device diagnostic algorithm, based on power draw of system 10, for example.

The application of the treatment algorithm 114 may include the control of multiple parameters such as temperature, time, cycling, pulsing, and ramp rates for cooling or thawing of treatment areas. In parallel with the treatment algorithm 114, one or more power monitoring algorithms 115 can be implemented. An appropriate needle assembly can then be mounted 116 to the handpiece, with the needle assembly optionally having a needle length, skin surface cooling chamber, needle array, and/or other components suitable for treatment of the target tissues. Simpler systems may include only a single needle type, and/or a first needle assembly mounted to the handpiece.

Pressure, heating, cooling, or combinations thereof may be applied 118 to the skin surface adjacent the needle insertion site before, during, and/or after insertion 120 and cryogenic cooling 122 of the needle and associated target tissue. Non-target tissue directly above the target tissue can be protected by directly conducting energy in the form of heat to the cladding on a proximal portion of the needle shaft during cooling. Upon completion of the cryogenic cooling cycle the needles will need additional "thaw" time 123 to thaw from the internally created cooling zone to allow for safe removal of the probe without physical disruption of the target tissues, which may include, but not be limited to nerves, muscles, blood vessels, or connective tissues. This thaw time can either be timed with the refrigerant valve shut-off for as short a time as possible, preferably under 15 seconds, more preferably under 5 seconds, manually or programmed into the controller to automatically shut-off the valve and then pause for a chosen time interval until there is an audible or visual notification of treatment completion.

Heating of the needle may be used to prevent unwanted skin damage using the apparatus and methods previously described. The needle can then be retracted 124 from the target tissue. If the treatment is not complete 126 and the needle is not yet dull 128, pressure and/or cooling can be applied to the next needle insertion location site 118, and the additional target tissue treated. However, as small gauge needles may dull after being inserted only a few times into the skin, any needles that are dulled (or otherwise determined to be sufficiently used to warrant replacement, regardless of whether it is after a single insertion, 5 insertions, or the like) during the treatment may be replaced with a new needle 116 before the next application of pressure/cooling 118, needle insertion 120, and/or the like. Once the target tissues have been completely treated, or once the cooling supply canister included in the self-contained handpiece is depleted, the used canister and/or needles can be disposed of 130. The handpiece may optionally be discarded.

In some embodiments of the present invention, a method of amputating an extremity of a patient is provided. Optionally, embodiments of the cryogenic cooling devices described above may be utilized in the amputation method described below.

Figure 15:
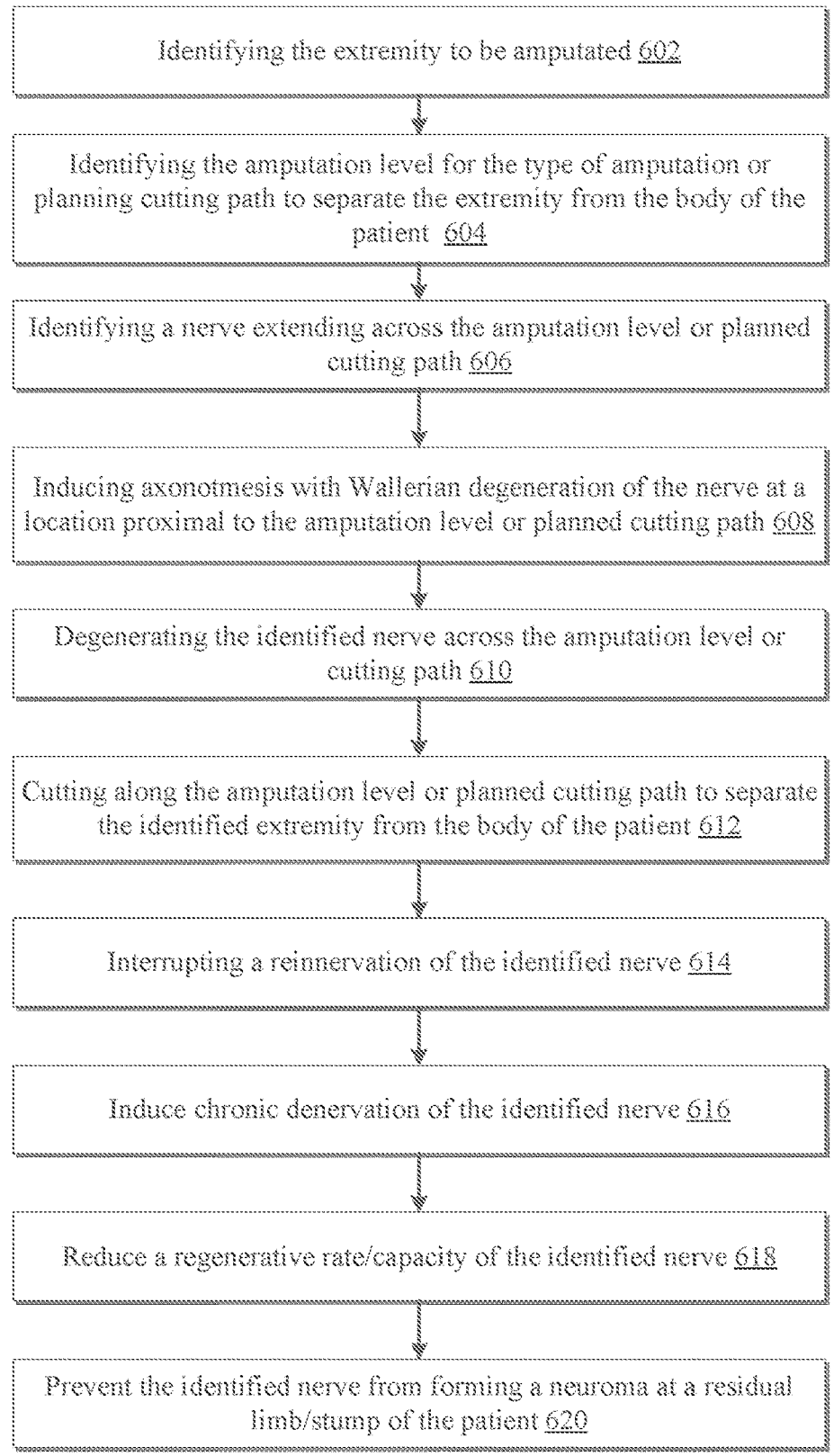
FIG. 15 is a flow chart illustrating an exemplary method for amputating an extremity of a patient.

FIG. 15 illustrates an exemplary method 600 for amputating an extremity of a patient. The method 600 may start by identifying the extremity of the patient to be amputated 602. After identifying the extremity of the patient to be amputated, an amputation level for the type of amputation may be identified or a cutting path may be planned 604 to separate the identified extremity from the body of the patient. A nerve extending across the amputation level or planned cutting path may be identified 606. Axonotmesis of the nerve may be induced 608 at a location proximal to the amputation level or planned cutting path. The identified nerve may degenerate across the amputation level or cutting path 610. The identified extremity may be separated from the body of the patient by cutting along the amputation level or planned cutting path 612. After amputation of the extremity, a regeneration of the identified nerve may be interrupted 614. The interruption of the regeneration of the identified nerve may induce chronic denervation of the identified nerve 616. A regenerative rate/capacity of the identified nerve 618 may be reduced. The identified nerve may be prevented from forming a neuroma at the residual stump of the patient 620.

The method 600 may be applicable to many body extremities that are to be amputated. Amputation surgery may be necessary if an injured or diseased limb is not expected to heal and if the patient's life is endangered as a result. Possible causes include circulation issues, infections, accidents, cancer, or a congenital malformation of the limb. In these cases, it is usually known well in advance that an amputation will become necessary. In contrast, sometimes it is necessary to amputate unexpectedly, for example due to a severe injury after an accident. The method 600 may be applicable to upper limb amputations: metacarpal amputation, wrist disarticulation, transradial amputation, elbow disarticulation, transhumeral amputation, shoulder disarticulation, forequarter amputation etc. Additionally, method 600 may be applicable to lower limb amputations: foot amputation, transtibial amputation, knee disarticulation, transfemoral amputation, hip disarticulation, hemipelvectomy, etc. The method 600 may also be carried out, as desired or needed, for the amputation of other portions of the body.

After identifying the extremity to be amputated 602, an amputation level may be determined and/or a cutting path may be planned 604 to separate the identified extremity from the body of the patient. The term amputation level may be used to describe the location at which the body part is amputated. The amputation level may be determined by the doctor before the operation and is based on the reason for the amputation. For planned interventions, a prosthetist may be consulted as well in order to identify which amputation level is suitable for subsequent fitting of the prosthesis. A cutting path may be planned based on the identified amputation level. For example, for a lower limb amputation, a transfemoral amputation may be prescribed 604 and an associated cutting path may be planned 604 that traverses the femur at an preferred height.

Figure 16:
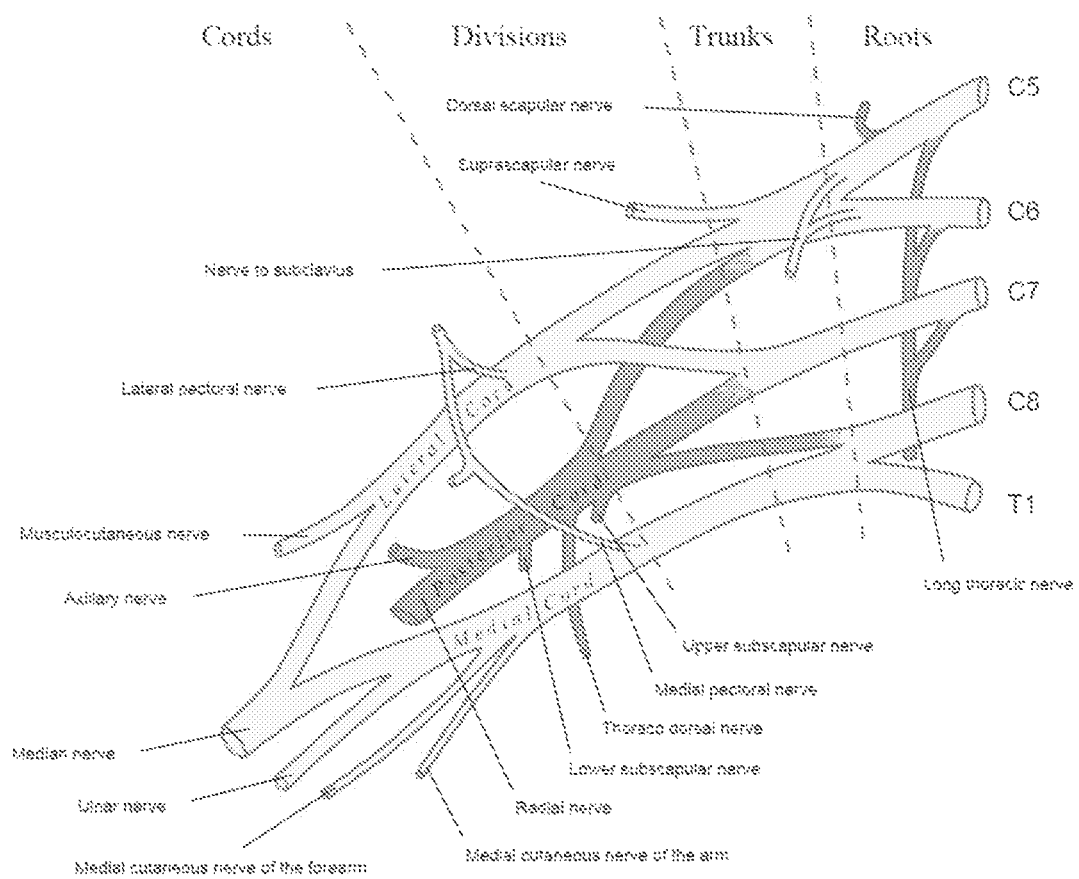
FIG. 16 illustrates nerves of the brachial plexus that may be targeted for treatment according to some embodiments of the present invention.
Figure 17A:
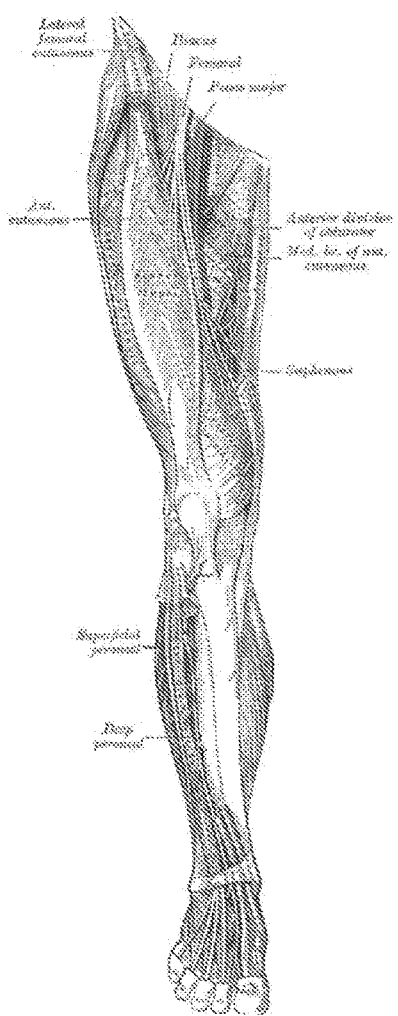
FIG. 17A and FIG. 17B illustrate nerves of the leg that may be targeted for treatment according to some embodiments of the present invention.
Figure 17B:
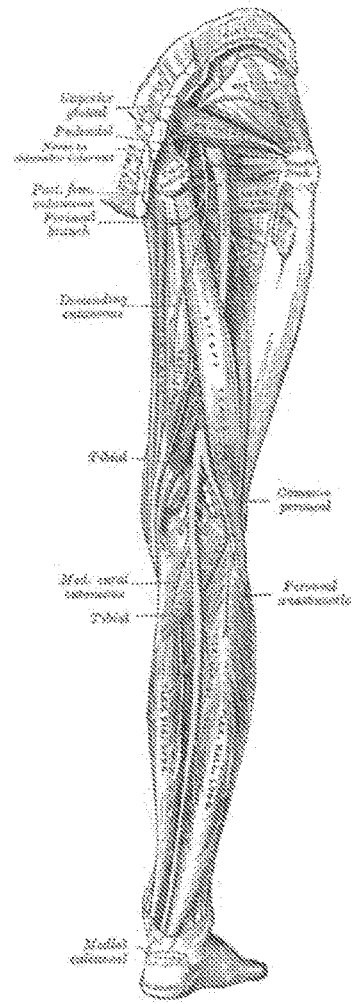

After identifying the type and level of amputation and/or planning an associated cutting path 604, one or more nerves extending across the amputation level or planned cutting path may be identified 606. For example, for an upper limb transradial amputation, one or more of the nerves of the brachial plexus, FIG. 16, may be identified for treatment such as the medial cutaneous nerve of the forearm, the ulnar nerve, radial nerve, the median nerve, etc. For a lower limb transtibial or transfemoral amputation, one or more nerves of leg, FIG. 17A-FIG. 17B, may be identified for treatment such as the sciatic nerve, tibial nerve, common peroneal nerve, superficial peroneal nerve, deep peroneal nerve, sural nerve, lateral cutaneous nerve of the calf, saphenous nerve, femoral nerve, etc.

After identifying one or more nerves extending across the identified amputation level or planned cutting path 606, axonotmesis of the nerve may be induced 608 at a location proximal to the amputation level or planned cutting path. Axonotmesis is a type of nerve injury that involves the loss of relative continuity of the axon and its covering myelin sheath but preservation of the connective tissue framework of the nerve at the treatment site and distal to the treatment site. Thus the axon and myelin sheath may be disrupted or otherwise damaged, but the endoneurium, perineurium, and epineurium may remain intact. This type of nerve damage may result in the loss of function of the nerve (motor or sensory) distal to the site of injury. Due to the loss in continuity of the axon, Wallerian degeneration may occur where the cell body of the nerve degenerates distal to the site of injury. After injury, the distal axonal skeleton disintegrates, and the axonal membrane breaks apart. The axonal degeneration is followed by degradation of the myelin sheath and infiltration by macrophages. The macrophages, accompanied by Schwann cells, serve to clear the debris from the degeneration. In many embodiments, the axonotmesis may be induced 608 using embodiments of the cryogenic cooling probes described above. Axonotmesis may be induced with interventions such as cryogenic cooling therapy. Alternatively, thermal ablation therapies that operate under controlled temperatures may be used to induce axonotmesis (e.g. radiofrequency, microwave, laser, ultrasound) while avoiding an irreversible nerve injury involving a disruption of connective nerve tissue. By disrupting the connective tissue of the nerve at the proximal point of treatment, an ablative treatment may have a lower incidence of neuroma formation with potential chronic pain resulting from the neuroma formation.

Thus, according to method 600, due to the axonotmesis at a location proximal to the amputation level or planned cutting path, the identified nerve may degenerate across the amputation level or cutting path 610 and distally from the amputation level or cutting path. Thereafter, the identified extremity may be separated from the body of the patient by cutting along the amputation level or planned cutting path 612. The amputation may proceed using known methods for removing and reforming tissue and dressing the wound. The amputation of the extremity transects the identified nerve at a transection location/site. After inducing axonotmesis, a proximal portion of the identified nerve that remains may sprout in a distal direction as part of the nerve's healing process. In many embodiments, the amputation 612 occurs prior to the regeneration of the identified nerve across the amputation level or planned cutting path. In such a method, only the connective tissue of the identified nerve is transected whereas the axon has already experienced degeneration across the amputation level or planned cutting path prior to amputation.

While method 600 is generally discussed as inducing axonotmesis prior to amputation, it should be understood that in other embodiments, the axonotmesis may be induced concurrently with the amputation of the extremity or shortly thereafter. If axonotmesis is induced after amputation, it may be beneficial to induce axonotmesis proximal to the site of nerve transection within a month after amputation (e.g., within a couple weeks, a week, or a day after amputation) such that neuroma formation by the transected nerve at the transection site may be prevented.

During the regenerative process of the nerve, the nerve may continue to regenerate along the nerve's remaining connective tissue in a distal direction from the site of injury (where the axonotmesis is induced) at a rate of about 1 mm to 2 mm per day. In some embodiments of the present invention, it may be beneficial, but not necessary, to interrupt the regeneration of the identified nerve 614. The reinnervation of the distal connective tissue of the identified nerve may be interrupted by re-inducing axonotmesis at a site proximal to the distal end of the regenerating nerve. For example, in some embodiments, the cryogenic cooling probes described above may be used to re-induce axonotmesis of the identified nerve. Optionally, a cooling treatment may be administered at about the site of the initial axonotmesis of the identified nerve. The interruption of the nerve's regeneration may occur over regular intervals for a period of time. For example, in some embodiments, the regeneration of the identified nerve may be interrupted anywhere from daily to as long as 4 week intervals (e.g., weekly intervals, biweekly intervals, etc.). Further, the regeneration may be interrupted over a period from 1 month to as long as 6 months (e.g., repeated treatments over 3 months). In some embodiments, interruption of the regeneration of the nerve may be provided by follow on repeat treatments. The repeat treatments prevent regeneration of the nerve at the transection site of the nerve. It should be understood that each repeat treatment does not need to occur at the precise site of the original treatment; but should occur along the length of the target nerve.

In some embodiments, repeated treatments may be applied to the target nerve at 4 week intervals over a 3 month period (or 12 week period), for example. A total of 3 monthly (or 4 week interval) treatments may occur over the three month period.

In a more aggressive approach, repeated treatments may be applied to the target nerve at 1 week intervals over a 3 month period. A total of 12 weekly treatments may occur over a 3 month period.

The interval timing may depend on distance to the transection site of the nerve from the site of inducing axonotmesis. As the nerve regeneration rate is about 1 mm to 2 mm per day, shorter distances between the site of axonotmesis (initial site or follow-on site) and the transection site of the nerve may benefit from shorter repeat treatment intervals so as to maintain a degeneration of the target nerve at the nerve's transection site while longer distances between the axonotmesis site and the transection site may allow for longer intervals. The repeated interruption of the regeneration of the identified nerve may induce chronic denervation of the identified nerve 616.

Figure 18:
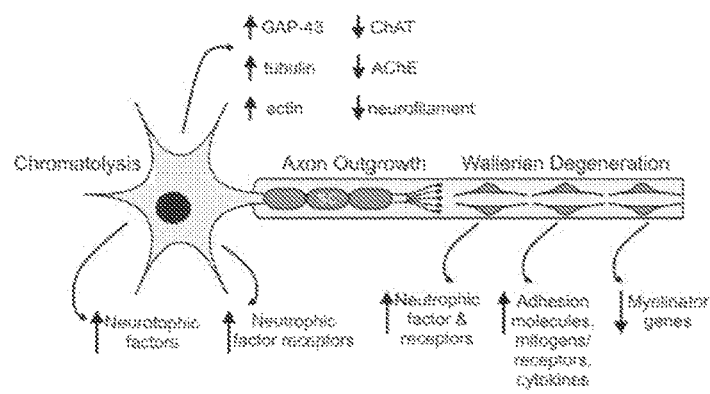
FIG. 18 illustrates nerve gene expression after nerve injury.

In some embodiments, the chronic denervation of the nerve reduces a regenerative rate/capacity of the identified nerve 618. After nerve injury, regeneration-associated genes (RAGs) are up-regulated transiently in the neurons while genes associated with normal synaptic transmissions are down-regulated, FIG. 18. Schwann cells in the degenerated nerve stump undergo proliferation during Wallerian degeneration and express many RAGs. The gene profiles support the outgrowth of axons, but the expression is short lived such that over time, the expression of RAGs is down-regulated and the capacity of the injured neurons to regenerate their axons and Schwann cells to support regeneration is diminished. Accordingly, in some embodiments of the present invention, it may be beneficial to delay regeneration of the identified nerve until the expression of RAGs is down-regulated and the regenerative rate or capacity of the nerve is sufficiently diminished. As stated above, the regeneration rate of a nerve may be about 1 mm to 2 mm per day. In some embodiments, the chronic denervation may reduce a regeneration rate of a nerve to less than 1 mm per day, to less than 0.5 mm per day, to less than 0.1 mm per day, less than 0.05 mm per day, or permanently disrupted by the chronic denervation (i.e., approximately 0 mm per day).

Advantageously, the disruption of the regeneration of the nerve after amputation may prevent the nerve from forming a neuroma at the transected end of the nerve in the residual stump of the patient 620. Neuromas may result of the normal nerve regrowth during the healing process. The lack of an axonal sheath at the residual limb may result in a chaotic pattern of regrowth forming a ball-like intertwined structure at the distal end of the transected nerve. The incidence of painful neuromas is thought to be between 10 to 25%. Limb pain from neuroma is often variable in intensity, of intermittent duration, with changeable qualities of aching, cramping or shooting. According to some embodiments, disruption of the regeneration of the nerve after amputation may prevent the nerve from extending to the residual limb of the patient and may thereby avoid the formation of a neuroma at the transected end of the nerve all together. Thus some embodiments of the invention may be directed to the prevention of the formation of one or more neuromas after amputation of an extremity of a patient or after transection of a nerve.

For example, FIGS. 19A-19D illustrate an amputation of a hand 704 of a patient 700 with an arm 702 according to method 600. Arm 702 may include a plurality of nerves 705, 706 extending down the length of the arm 702 and innervating various portions of the arm 702. An amputation of a hand 704 of the arm 702 may be planned and a location of inducing axonotmesis may be based thereon.

After planning the amputation of the hand 704, axonotmesis of nerves 705, 706 may be induced at locations 708, 710, respectively. As explained above, the inducement of axonotmesis of nerves 705, 706 may be carried out using embodiments of the therapeutic cryoprobes described above. Additionally, in many embodiments, the inducement of axonotmesis of nerves 705, 706 may be performed prior to amputation of hand 704. It is understood however, that in other embodiments, axonotmesis is performed concurrently with the amputation of hand 704 or shortly after amputation of hand 704.

Figure 19A:
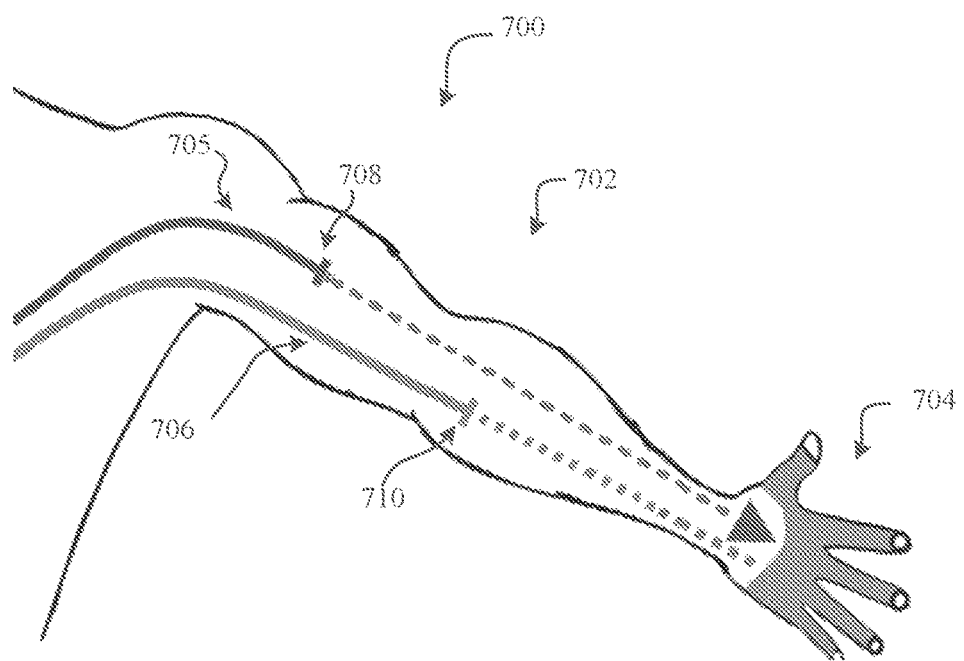
FIGS. 19A-19D illustrate an amputation of a hand of a patient according to some embodiments of the invention.
Figure 19B:
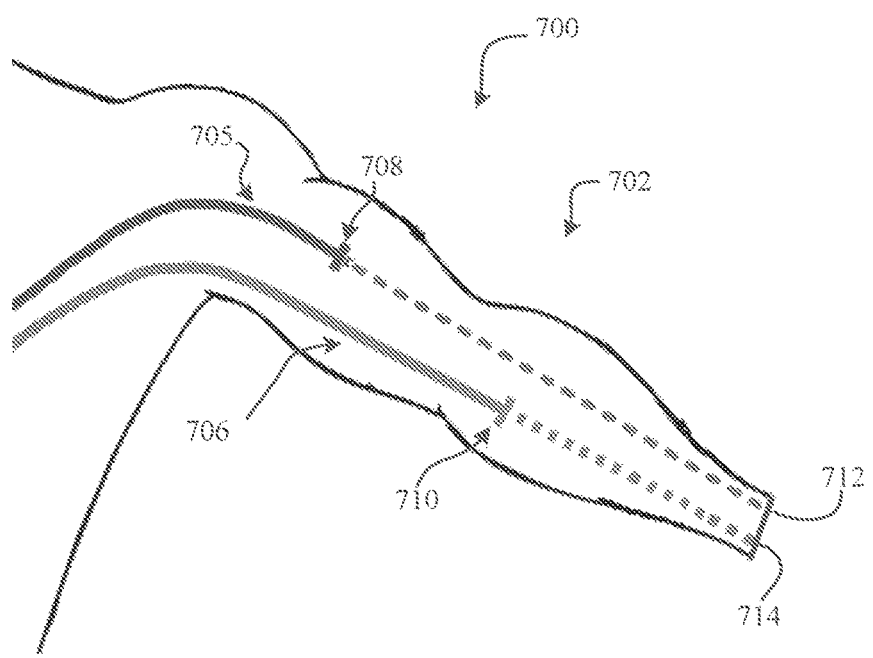

As illustrated in FIG. 19A, degeneration of the nerves 705, 706 (dotted lines) occurs distal from the site of inducing axonotmesis 708, 710. As illustrated in FIG. 19B, after inducing axonotmesis of the target nerve(s) and amputation of the hand 704, the nerves 705, 706 are degenerated at the transection sites 712, 714 at the residual limb of the patient according to the method 600.

Figure 19C:
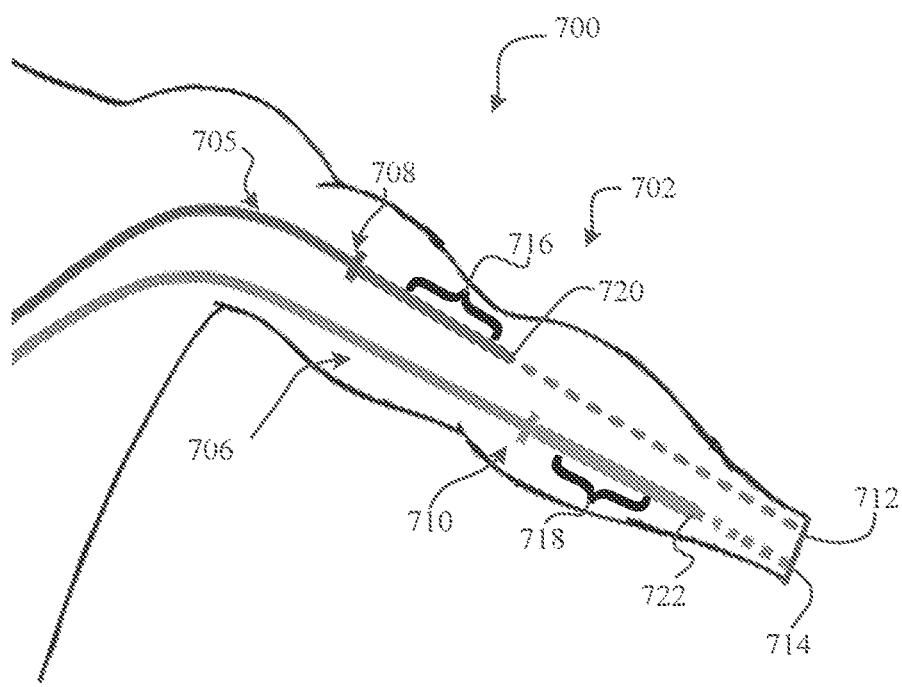

In some embodiments, the method 600 may proceed by interrupting a regeneration process of the one or more transected nerves 705, 706. For example, as illustrated in FIG. 19C, a portion 716, 718 of each nerve 705, 706 may regenerate distally from the initial locations 708, 710 where axonotmesis was induced after a period of time. Nerves of the peripheral nervous system typically regenerate at 1-2 mm per day. The regeneration process may be interrupted by reinducing axonotmesis at locations 708, 710 (or at any location proximal to distal ends 720, 722 of the nerves 705, 706) at intervals and over a period of time. Preferably, the repeated induction of axonotmesis is performed prior to the regeneration of the distal ends 720, 722 of the nerves 705, 706 to the transected site 712, 714. As the distance between the location 710 and transected site 714 is shorter than a distance between location 708 and transected site 712, nerve 706 may benefit from a shorter repeat treatment interval compared to a repeat treatment interval of nerve 705. Thus, the interval for repeat treatments may be elected based on a distance between the site of inducing axonotmesis (initial or follow-on) and the site of transection where shorter intervals are preferred for shorter distances and longer intervals are allowed for longer distances.

Figure 19D:
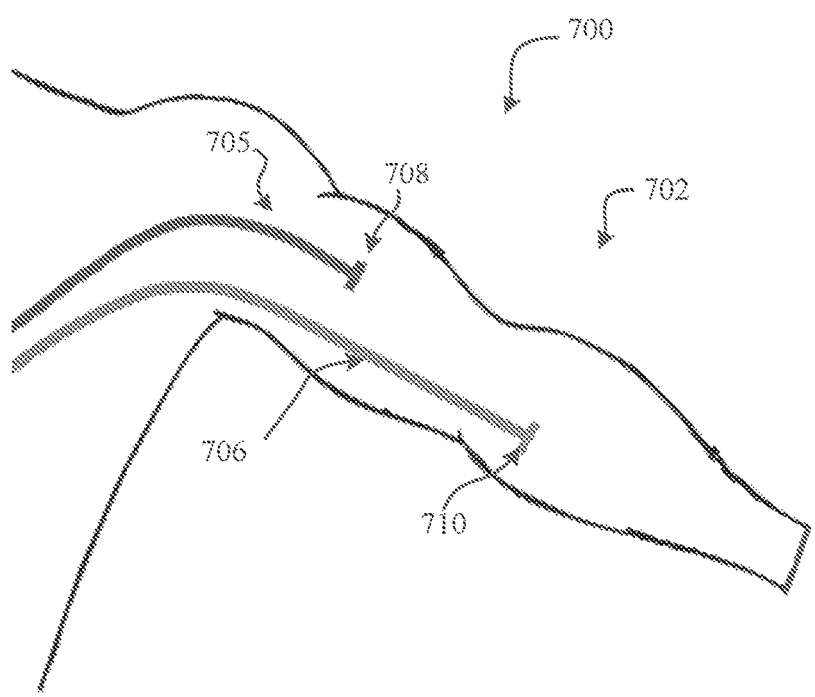

After a number of interruptions of the regeneration of nerves 705, 706 over a period of time, chronic denervation may occur and a regeneration rate of the nerves 705, 706 may be reduced (e.g., reduced to less than 1 mm per day, less than 0.5 mm per day, less than 0.25 mm per day, or permanently deactivated). For example, FIG. 19D illustrates nerves 705, 706 after chronic denervation where the nerves 705, 706 effectively do not regenerate toward the distal end of the arm 702. Advantageously, such a method may prevent the nerves 705, 706 from forming a neuroma at the transected ends 712, 714 of nerves 705, 706.

While the method described above is in the context of amputation, it should be understood that this is only used as one example of such a planned surgical intervention that may involve nerve transection or injury. Embodiments of the invention are not limit to amputation alone. Embodiments of the present invention may be applied to any medical intervention where nerve transection or injury may result and the methods and device described herein may be used proximal to the point of transection or injury to avoid (or reduce) the formation of a neuroma.

Figure 20A:
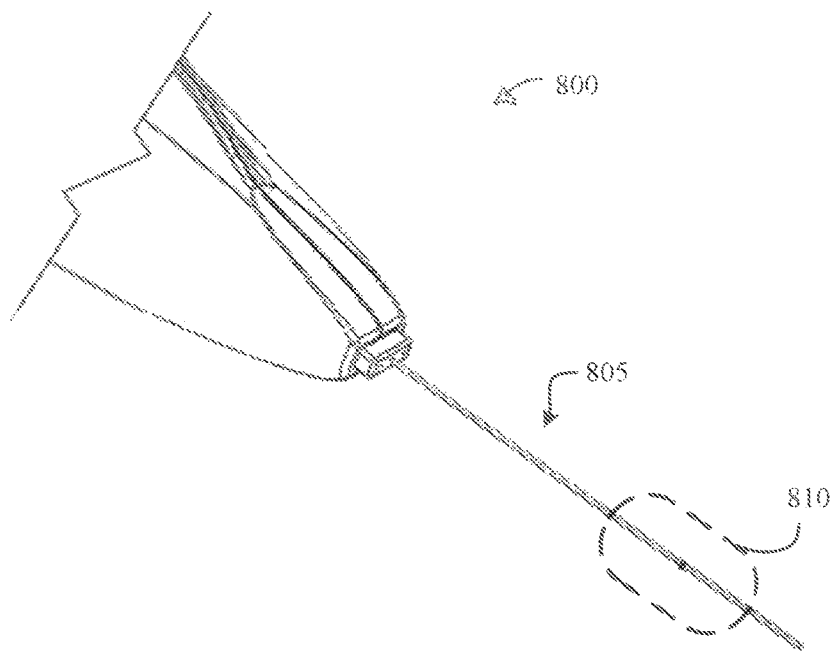
FIGS. 20A-20B illustrate an exemplary system according to some embodiments of the invention.
Figure 20B:
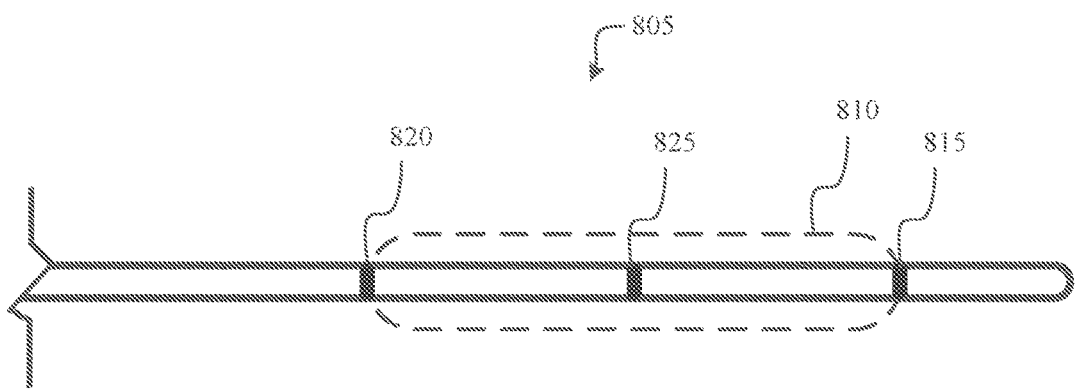

FIGS. 20A-20B illustrate a distal end of an exemplary cryoprobe 800 for treating a nerve according to some embodiments. The probe 800 may have a needle 805 extending distally that is configured to generate a cryozone 810. In some embodiments, as illustrated in the close up of needle 805 in FIG. 20B, the needle 805 may include one or more marks along the length of the needle. The one or more marks may comprise a mark 815 for marking a distal end of the cryozone 810 that is generated by the probe 800, a mark 820 for marking a proximal end of the cryozone 810 that is generated by the probe 800, and/or a mark 825 for marking a center of a the cryozone 810 that is generated by the probe 800.

Figure 21:
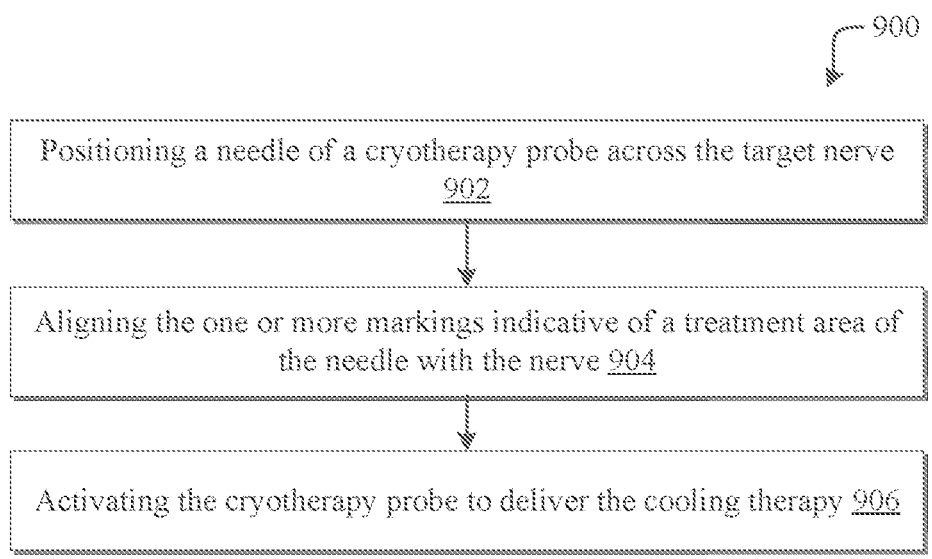
FIG. 21 illustrates an exemplary method of treating a nerve according to some embodiments of the invention.

The marks 815, 820, 825 may be utilized for visually aligning the needle 805 of a probe 800 with a target nerve. For example, FIG. 21 illustrates an exemplary method 900 of treating a nerve according to some embodiments. At step 902, a needle of the cryotherapy probe is positioned across the target nerve. The one or more markings indicative of a treatment area (e.g., marks 815, 820, 825) of the needle may be aligned with the nerve 904. After alignment, the cryotherapy probe may be activated to deliver the cooling therapy 906.

In some embodiments, the needle may be provided with an echogenic coating that makes the needle more visible under ultrasound imaging. For example, in some embodiments, the entire length of the needle may be provided with an echogenic coating. Alternatively, the one or more of the marks 815, 820, 825, may be provided with an echogenic coating such that the distal end, proximal end, or center of the cryozone associated with the needle is visible under ultrasound imaging. In other embodiments, the one or more marks may be provided by a lack of echogenic coating. For example, in some embodiments, the length of the needle may be provided with an echogenic coating except for at the one or more marks 815, 820, 825, such that when viewed under ultrasound guidance, the distal, proximal, or center of the cryozone would be associated with the portion of the needle without the echogenic coating. Alternatively, the length of the needle may be provided with the echogenic coating that ceases at the center of the associated cryozone, such that when viewed under ultrasound guidance, the distal end of the echogenic coating would be associated with a center of a cryozone of the needle.

Long needles may be used in some embodiments (e.g., 8-15 mm, 20 mm, 90 mm etc.). Longer needles may require a smaller gauge (larger diameter) needle so they have sufficient rigidity to maintain consistent spacing when placed deep in the tissue, but not so large as to create significant mechanical injury to the skin and tissue when inserted (e.g., greater than 20 ga). Alternate configurations of the device may have two or more needles spaced generally 3-5 mm apart of lengths ranging from up to 20 mm or greater, typically of 25 gauge or 23 gauge. Single needle configurations may be even longer (e.g., 90 mm) for reaching target tissues that are even deeper (e.g., >15 mm or so below the dermis). Longer needle devices (e.g., >10 mm) may not need active heating of the skin warmer and/or cladding found in designs using shorter needle(s) as the cooling zone may be placed sufficiently deep below the dermis to prevent injury. In some embodiments, devices with single long needle configurations may benefit from active nerve location such as ultrasound or electrical nerve stimulation to guide placement of the needle. Further, larger targets may require treatment from both sides to make sure that the cold zone created by the needle fully covers the target. Adjacent treatments placing the needle to either side of a nerve during two successive treatment cycles may still provide an effective treatment of the entire nerve cross-section.

In some situations, a probe with multiple spaced apart needles may be preferable (e.g., 2, 3, 4 or more). A device employing multiple needles may decrease the total treatment duration by creating larger cooling zones. Further, a multi-needle device may be configured to provide continuous cooling zones between the spaced apart needles. In some embodiments, the needles may be spaced apart by 1-5 mm. The spacing may be dependent on the type of tissue being targeted. For example, when targeting a nerve, it may be preferable to position the nerve between the two or more needles so that cooling zones are generated on both sides of the nerve. Treating the nerve from both sides may increase the probability that the entire cross-section of the nerve will be treated. For superficial peripheral nerves, the nerves may be at depths ranging from 2-6 mm and may be smaller in diameter, typically <2 mm. Accordingly, devices for treating superficial peripheral nerves may comprises two or more 27 gauge needles spaced ≤2 mm apart and having typical lengths less than 7 mm (e.g., 6.9 mm); however longer needles may be required to treat the full patient population in order to access patients with altered nerve anatomy or patients with higher amounts of subcutaneous tissue such as those with high BMIs.

A treatment cycle may comprise a 10 second pre-warm phase, followed by a 60 second cooling phase, followed thereafter by a 15 second post-warm phase with 40° C. skin warmer throughout. It should be understood that other treatment cycles may be implemented. In some embodiments, a pre-warming cycle can range from 0 to up to 30 seconds, preferably 5-15 seconds sufficient to pre-warm the cryoprobe and opposing skin. Treatment cooling may range from 5-120 seconds, preferably 15-60 seconds based on the flow rate, geometry of the cryoprobe, size of the therapy zone, size of the target nerve or tissue and the mechanism of action desired. Post warming can range from 0-60 seconds, preferably 10-15 seconds sufficient to return the cryoprobe to a steady state thermal condition and possibly to free the cryoprobe needle(s) from the frozen therapy zone (e.g., at least 0° C.) prior to removing the cryoprobe needles. For example, in some embodiments, devices with 6.9 mm long cladded needles may be warmed with a 30° C. heater. The treatment cycle may comprise a 10 second pre-warm phase, a 35 second cooling phase, and a 15 second post-warm phase. Advantageously, such a treatment cycle may make an equivalent cryozone as the treatment cycle used in the study in a shorter amount of time (e.g., a 35 second cooling phase compared to a 60 second cooling phase).

In some embodiments, treatment devices and treatment cycles may be configured to deliver a preferred cryozone volume. For example, in some embodiments, devices and treatment cycles may be configured to generate cryozones (defined by the 0 degree isotherm) having a cross-sectional area of approximately 14-55 $mm^2$ (e.g., 27 $mm^2$). Optionally, the devices and treatment cycles may be configured to generate cryozones having a volume of approximately 65-125 $mm^3$ (e.g., 85 $mm^3$).

Accordingly, in some embodiments, treatment cycles may be configured with cooling phases ranging between 15-75 seconds (e.g., 30 seconds, 35 seconds, 40 seconds, 45 seconds, etc.) depending on cooling fluid flow rates, warming phase durations, warming phase temperature, number of cooling needles, needle spacing, or the like in order to generate a desired cryozone. Similarly, treatment cycles may be configured with warming phases operating a temperatures ranging between 10-45° C. depending on the length of cooling phases, number of needles, needle spacing, etc. in order to generate a desired cryozone. Generally, with higher degree warming phases, the duration of the pre-warm phase and the cooling phase will be longer, however the post-warm phase duration may be reduced. In some embodiments the temperature can be set to one temperature during the pre-warm phase, another temperature during the cooling phase, and a third temperature during the post-warm phase.

In some embodiments, devices may be configured to limit flow rate of a cooling fluid to approximately 0.34-0.80 SLPM (gas phase). Optionally, in some embodiments, it may be preferable to configure the device and the treatment cycle to maintain the tip a less than −55° C. during cooling phases. In some embodiments, it may be preferable to configure the device and the treatment cycle to have the tip return to at least 0° C. at the end of the post-warm phase so as to ensure the device may be safely removed from the tissue after the treatment cycle.

While generally describing treatment cycles as including pre-heating/warming phases, it should be understood that other treatment cycles may not require a pre-heating/warming phase. For example, larger needle devices (e.g., 30-90 mm) may not require a pre-heat/warm phase. Larger needles may rely on the body's natural heat to bring the needle to a desired temperature prior to a cooling phase.

In some embodiments of the present invention, treatment guidance can rely on rigid or boney landmarks because they are less dependent upon natural variations in body size or type, e.g. BMI. Soft tissues, vasculature and peripheral nerves pass adjacent to the rigid landmarks because they require protection and support. The target nerve to relieve pain can be identified based on the diagnosis along with patients identifying the area of pain, biomechanical movements that evoke pain from specific areas, palpation, and diagnostic nerve blocks using an temporary analgesic (e.g. 1-2% Lidocaine). Target nerve (tissue) can be located by relying on anatomical landmarks to indicate the anatomical area through which the target nerve (tissue) reside. Alternatively, nerve or tissue locating technologies can be used. In the case of peripheral nerves, electrical stimulation or ultrasound can be used to locate target nerves for treatment. Electrical nerve stimulation can identify the nerve upon stimulation and either innervated muscle twitch in the case of a motor nerve or altered sensation in a specific area in the case of a sensory nerve. Ultrasound is used to visualize the nerve and structures closely associated with the nerve (e.g. vessels) to assist in placing the cryoprobe in close proximity to the target nerve. By positioning the patient's skeletal structure in a predetermined position (e.g. knee bent 30 degrees or fully extended), one can reliably position the bones, ligaments, cartilage, muscle, soft tissues (including fascia), vasculature, and peripheral nerves. External palpation can then be used to locate the skeletal structure and thereby locate the pathway and relative depth of a peripheral nerve targeted for treatment.

A treatment of peripheral nerve tissue to at least −20° C. for greater than 10 seconds (e.g., at least 20 seconds preferably) may be sufficient to trigger 2nd degree Wallerian degeneration of the axon and mylinated sheath. Conduction along the nerve fibers is stopped immediately following treatment. This provides immediate feedback as to the location of the target peripheral nerve or associated branches when the associated motion or sensation is modified. This can be used to refine rigid landmark guidance of future treatments or to determine whether addition treatment is warranted.

By using rigid landmarks, one may be able to direct the treatment pattern to specific anatomical sites where the peripheral nerve is located with the highest likelihood. Feedback from the patient immediately after each treatment may verify the location of the target peripheral nerve and its associated branches. Thus, it should be understood that in some embodiments, the use of an electronic nerve stimulation device to discover nerve location is not needed or used, since well-developed treatment zones can locate target nerves. This may be advantageous, due the cost and complexity of electronic nerve stimulation devices, which are also not always readily available.

In alternative embodiments of the invention, one could use an electronic nerve stimulation device (either transcutaneous or percutaneous) to stimulate the target peripheral nerve and its branches. With transcutaneous electric nerve stimulation (TENS) the pathway of the nerve branch can be mapped in an X-Y coordinates coincident with the skin surface. The Z coordinate corresponding to depth normal to the skin surface can be inferred by the sensitivity setting of the electrical stimulation unit. For example, a setting of 3.25 mA and pulse duration of 0.1 ms may reliably stimulate the frontal branch of the temporal nerve when it is within 7 mm of the skin surface. If a higher current setting or longer pulse duration is required to stimulate the nerve, then the depth may be >7 mm. A percutaneous electrical nerve stimulator (PENS) can also be used to locate a target peripheral nerve. Based on rigid anatomical landmarks, a PENS needle can be introduced through the dermis and advanced into the soft tissues. Periodic stimulating pulses at a rate of 1-3 Hz may be used to stimulate nerves within a known distance from the PENS needle. When the target nerve is stimulated, the sensitivity of the PENS can be reduced (e.g. lowering the current setting or pulse duration) narrowing the range of stimulation. When the nerve is stimulated again, now within a smaller distance, the PENS sensitivity can be reduced further until the nerve stimulation distance is within the therapy zone dimensions. At this point, the PENS needle can be replaced with the focused cold therapy needle(s) and a treatment can be delivered. The PENS and focused cold therapy needles can be introduced by themselves or through a second larger gage needle or cannula. This may provide a rigid and reproducible path when introducing a needle and when replacing one needle instrument with another. A rigid pathway may guide the needle to the same location by preventing needle tip deflection, which could lead to a misplaced therapy and lack of efficacy.

While many of the examples disclosed herein related to puncturing the skin in a transverse manner to arrive at a target nerve, other techniques can be used to guide a device to a target nerve. For example, insertion of devices can be made parallel to the surface of the skin, such that the (blunted) tip of the device glides along a particular fascia to arrive at a target sensory nerve. Such techniques and devices are disclosed in U.S. Pub. No. 2012/0089211, the entirety of which is incorporated by reference. Possible advantages may include a single insertion site, and guidance of a blunt tip along a layer common with the path or depth of the target nerve. This technique may be a position-treatment—thaw, reposition treatment, thaw, etc.

One or more computing devices may be adapted to provide desired functionality by accessing software instructions rendered in a computer-readable form. When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including but not limited to application-specific circuits. Combinations of computer-executed software and hard-wired logic or other circuitry may be suitable as well.

Embodiments of the methods disclosed herein may be executed by one or more suitable computing devices. Such system(s) may comprise one or more computing devices adapted to perform one or more embodiments of the methods disclosed herein. As noted above, such devices may access one or more computer-readable media that embody computer-readable instructions which, when executed by at least one computer, cause the at least one computer to implement one or more embodiments of the methods of the present subject matter. Additionally or alternatively, the computing device(s) may comprise circuitry that renders the device(s) operative to implement one or more of the methods of the present subject matter.

Any suitable computer-readable medium or media may be used to implement or practice the presently-disclosed subject matter, including but not limited to, diskettes, drives, and other magnetic-based storage media, optical storage media, including disks (e.g., CD-ROMS, DVD-ROMS, variants thereof, etc.), flash, RAM, ROM, and other memory devices, and the like.

The subject matter of embodiments of the present invention is described here with specificity, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A method of preventing neuroma formation in nerve tissue associated with transection of a nerve during a medical intervention, the method comprising:
   identifying a nerve extending across a transection path which separates a distal portion of the nerve from a proximal portion of the nerve;
   administering a first cooling therapy to the identified nerve at a location proximal to the transection path so as to degenerate the identified nerve across the transection path prior to, during, or within a predetermined time after surgical transection along the transection path to transect the identified nerve, wherein cooling the identified nerve prevents or reduces neuroma formation at a transected end of the nerve after transection of the nerve; and
   selecting an interval for a repeated application of a second cooling therapy based on a distance between the location proximal to the transection path where degeneration was induced and the transection path, wherein shorter intervals are selected as the distance decreases and longer intervals are selected as the distance increases.

2. The method of claim 1, wherein the repeated application of the second cooling therapy is configured to target a regeneration of the identified nerve at one or more locations along a length of the identified nerve and proximal to the regeneration of the nerve extending toward a location of the transection of the identified nerve.

3. The method of claim 2, wherein the repeated application of the second cooling therapy reduces an expression of nerve growth factors.

4. The method of claim 2, wherein the repeated application of the second cooling therapy repeatedly disrupts reinnervation, regeneration, or growth of an axon of the identified nerve thereby reducing a regenerative rate of the identified nerve so as to prevent or reduce neuroma formation.

5. The method of claim 4, wherein the repeated application of the second cooling therapy to disrupt the reinnervation, regeneration, or growth of the identified nerve induces chronic denervation of the identified nerve.

6. The method of claim 4, wherein the regenerative rate of the identified nerve is reduced to less than 1 mm per day.

7. The method of claim 6, wherein the regenerative rate of the identified nerve is reduced to less than 0.5 mm per day.

8. The method of claim 1, wherein administering the first cooling therapy to the identified nerve comprises:
   positioning a needle of a cryotherapy probe across the identified nerve;
   aligning visual indicia of the needle of the cryotherapy probe with the nerve, the visual indicia being indicative of a treatment area along a length of the needle; and
   activating the cryotherapy probe to deliver the first cooling therapy.

9. The method of claim 8, wherein the visual indicia comprise a marker identifying a distal end of the treatment area along the length of the needle.

10. The method of claim 8, wherein the visual indicia comprise a marker identifying a proximal end of the treatment area along the length of the needle.

11. The method of claim 8, wherein the visual indicia comprise a marker identifying a center of the treatment area along the length of the needle.

12. The method of claim 8, wherein the length of the needle is at least 10 mm.

13. The method of claim 8, wherein administering the first cooling therapy to the nerve is performed without medical imaging.

14. The method of claim 8, wherein the length of the needle is at least 6 mm.

15. The method of claim 1, wherein administering the first cooling therapy to the nerve comprises: positioning a needle of a cryotherapy probe along a length of the identified nerve and activating the cryotherapy probe to deliver the first cooling therapy.

16. The method of claim 1, wherein the identified nerve is a peripheral nerve.

17. The method of claim 1, wherein the medical intervention comprises a surgical amputation of a body extremity of a body of a patient and wherein surgically transecting along the transection path separates the body extremity from the body of the patient.

18. The method of claim 17, wherein surgically transecting along the transection path to separate the body extremity from the body of the patient is performed after degeneration of the identified nerve across the transection path.

19. The method of claim 1, wherein the repeated application of the second cooling therapy is configured to target a regeneration of the identified nerve at one or more locations along a length of the identified nerve, wherein the repeated application of the second cooling therapy is administered over a period of one month to three months before or after the transection of the nerve.

20. The method of claim 1, wherein the repeated application of the second cooling therapy is configured to target a regeneration of the identified nerve at one or more locations along a length of the identified nerve, wherein the repeated application of the second cooling therapy is applied between a daily interval and a four week interval.

21. The method of claim 1, wherein the first cooling therapy is administered after surgically transecting and within a month after transection.

22. A method of transecting a nerve extending to a target tissue, the method comprising:
degenerating a portion of the nerve by treating the nerve at a treatment location along the nerve, wherein the treatment degenerates an axon of the nerve distal to the treatment location while preserving a connective tissue framework of the nerve;
transecting the preserved connective tissue framework of the nerve at a transection location distal to the treatment location;
selecting an interval for a repeated disruption of a regeneration of the nerve based on a distance between the treatment location and the transection location, wherein shorter intervals are selected as the distance decreases and longer intervals are selected as the distance increases; and
repeatedly disrupting the regeneration of the nerve at the selected interval for a period of time so as to induce chronic denervation of the nerve, wherein the chronic denervation of the nerve reduces a regenerative rate of the nerve and delays neuroma formation at the transection location of the nerve.

23. The method of claim 22, wherein repeatedly disrupting the regeneration of the nerve comprises repeatedly applying cooling therapy to the nerve at a location proximal to the target tissue.

24. The method of claim 23, wherein the repeated application of cooling therapy is administered over a period of one month to three months after the transection of the nerve.

25. The method of claim 24, wherein the repeated application of cooling therapy reduces an expression of nerve growth factors.

26. The method of claim 23, wherein the repeated application of cooling therapy is applied between a daily interval and a four week interval.

27. The method of claim 23, wherein the cooling therapy comprises:
positioning a needle of a cryotherapy probe across the nerve;
aligning visual indicia of the needle of the cryotherapy probe with the nerve, the visual indicia being indicative of a treatment area along a length of the needle, wherein the length of the needle is at least 6 mm; and
activating the cryotherapy probe to deliver the cooling therapy.

28. The method of claim 22, wherein treating the nerve at the treatment location along the nerve while preserving a connective tissue framework of the nerve comprises applying thermal ablation therapy with a radiofrequency, ultrasound, microwave, or laser treatment of the nerve.

29. The method of claim 22, wherein treating the nerve at the treatment location along the nerve while preserving a connective tissue framework of the nerve comprises applying a cooling therapy using a cryogenic cooling device.

30. The method of claim 22, wherein the preserved connective tissue framework of the nerve is transected with a surgical amputation of a body extremity of a patient.

* * * * *